United States Patent
Glenn, Jr. et al.

(10) Patent No.: US 8,349,341 B2
(45) Date of Patent: *Jan. 8, 2013

(54) POROUS, DISSOLVABLE SOLID SUBSTRATE AND A SURFACE RESIDENT COATING OF CATIONIC SURFACTANT CONDITIONER

(75) Inventors: Robert Wayne Glenn, Jr., Liberty, OH (US); Kathleen Mary Kaufman, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 20 days.

This patent is subject to a terminal disclaimer.

(21) Appl. No.: 12/962,905

(22) Filed: Dec. 8, 2010

(65) Prior Publication Data

US 2011/0189247 A1 Aug. 4, 2011

Related U.S. Application Data

(60) Provisional application No. 61/267,702, filed on Dec. 8, 2009.

(51) Int. Cl.
*A61K 8/02* (2006.01)
*C08J 7/04* (2006.01)
*B05D 3/00* (2006.01)

(52) U.S. Cl. .................. 424/401; 427/532
(58) Field of Classification Search .......... None
See application file for complete search history.

(56) References Cited

U.S. PATENT DOCUMENTS

| | | |
|---|---|---|
| 2,356,168 A | 8/1944 | Mabley |
| 2,396,278 A | 3/1946 | Lind |
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,658,072 A | 11/1953 | Kosmin |
| 2,694,668 A | 11/1954 | Fricke |
| 2,809,971 A | 10/1957 | Bernstein |
| 3,152,046 A | 10/1964 | Kapral |
| 3,236,733 A | 2/1966 | Karsten |
| 3,321,425 A | 5/1967 | Blau |
| 3,332,880 A | 7/1967 | Kessler |
| 3,426,440 A | 2/1969 | Shen |
| 3,489,688 A | 1/1970 | Pospischil |
| 3,653,383 A | 4/1972 | Wise |
| 3,695,989 A | 10/1972 | Albert |
| 3,753,196 A | 8/1973 | Kurtz |
| 3,761,418 A | 9/1973 | Parran, Jr. |
| 3,929,678 A | 12/1975 | Laughlin |
| 3,967,921 A | 7/1976 | Haberli |
| 4,020,156 A | 4/1977 | Murray |
| 4,051,081 A | 9/1977 | Jabs |
| 4,089,945 A | 5/1978 | Brinkman |
| 4,149,551 A * | 4/1979 | Benjamin et al. ............. 132/200 |
| 4,196,190 A | 4/1980 | Gehman |
| 4,197,865 A | 4/1980 | Jacquet |
| 4,206,196 A * | 6/1980 | Davis ............. 424/401 |
| 4,217,914 A | 8/1980 | Jacquet |
| 4,272,511 A | 6/1981 | Papantoniou |
| 4,323,683 A | 4/1982 | Bolich, Jr. |
| 4,345,080 A | 8/1982 | Bolich, Jr. |
| 4,379,753 A | 4/1983 | Bolich, Jr. |
| 4,381,919 A | 5/1983 | Jacquet |
| 4,422,853 A | 12/1983 | Jacquet |
| 4,470,982 A | 9/1984 | Winkler |
| 4,507,280 A | 3/1985 | Pohl |
| 4,529,586 A | 7/1985 | De Marco |
| 4,565,647 A | 1/1986 | Llenado |
| 4,663,158 A | 5/1987 | Wolfram |
| 4,710,374 A | 12/1987 | Grollier |
| 4,822,613 A | 4/1989 | Rodero |
| 4,885,107 A | 12/1989 | Wetzel |
| 4,976,953 A | 12/1990 | Orr |
| 4,990,280 A | 2/1991 | Thorengaard |
| 5,055,384 A | 10/1991 | Kuhnert |
| 5,061,481 A | 10/1991 | Suzuki |
| 5,062,889 A | 11/1991 | Hohl |
| 5,094,853 A | 3/1992 | Hagarty |
| 5,100,657 A | 3/1992 | Ansher-Jackson |
| 5,100,658 A | 3/1992 | Bolich, Jr. |
| 5,104,646 A | 4/1992 | Bolich, Jr. |
| 5,106,609 A | 4/1992 | Bolich, Jr. |
| 5,166,276 A | 11/1992 | Hayama |
| 5,220,033 A | 6/1993 | Kamei |
| 5,261,426 A * | 11/1993 | Kellett et al. ............. 132/108 |
| 5,280,079 A | 1/1994 | Allen |
| RE34,584 E | 4/1994 | Grote |

(Continued)

FOREIGN PATENT DOCUMENTS

| | | |
|---|---|---|
| CN | 1138091 A | 12/1996 |
| CN | 1219388 A | 6/1999 |
| CN | 1268558 A | 10/2000 |
| CN | 1357613 A | 7/2002 |
| CN | 1530431 A | 9/2004 |
| CN | 1583991 A | 2/2005 |
| DE | 19607851 A1 | 9/1997 |
| DE | 10331767 A1 | 2/2005 |
| EP | 609808 A1 | 8/1994 |
| EP | 0858828 A1 | 8/1998 |

(Continued)

OTHER PUBLICATIONS

U.S. Appl. No. 13/440,475, filed Apr. 5, 2012, Granberg et al.
U.S. Appl. No. 13/597,539, filed Aug. 29, 2012, Glenn, Jr. et al.
U.S. Appl. No. 13/561,298, Jul. 30, 2012, Glenn, Jr. et al.
T. Hildebrand, P. Rüegsegger. "Quantification of bone microarchitecture with the structure model index." Computer Methods in Biomechanics and Biomedical Engineering 1997; 1:15-23.
Vesterby, A.; Star volume in bone research. A histomorphometric analysis of trabecular bone structure using vertical sections; Anat Rec.; Feb. 1993; 235(2): 325-334.

(Continued)

*Primary Examiner* — Robert A Wax
*Assistant Examiner* — Olga V Tcherkasskaya
(74) *Attorney, Agent, or Firm* — Angela K. Haughey

(57) ABSTRACT

The present invention relates to hair care compositions, especially those hair care compositions in the form of a hair care article that is a porous dissolvable solid substrate. The porous dissolvable solid substrate has a surface resident coating comprising the cationic surfactant conditioner active that can provide a conditioning benefit.

26 Claims, 4 Drawing Sheets

U.S. PATENT DOCUMENTS

| | | | |
|---|---|---|---|
| 5,391,368 A | 2/1995 | Gerstein | |
| 5,409,703 A | 4/1995 | McAnalley | |
| 5,429,628 A | 7/1995 | Trinh | |
| 5,457,895 A | 10/1995 | Thompson | |
| 5,476,597 A | 12/1995 | Sakata | |
| 5,580,481 A | 12/1996 | Sakata | |
| 5,582,786 A | 12/1996 | Brunskill | |
| 5,660,845 A | 8/1997 | Trinh | |
| 5,672,576 A | 9/1997 | Behrens | |
| 5,674,478 A | 10/1997 | Dodd | |
| 5,750,122 A | 5/1998 | Evans | |
| 5,780,047 A | 7/1998 | Kamiya | |
| 5,955,419 A | 9/1999 | Barket, Jr. | |
| 5,976,454 A | 11/1999 | Sterzel et al. | |
| 6,010,719 A | 1/2000 | Remon | |
| 6,106,849 A | 8/2000 | Malkan | |
| 6,177,391 B1 | 1/2001 | Zafar | |
| 6,200,949 B1 | 3/2001 | Reijmer | |
| 6,458,754 B1 | 10/2002 | Velazquez | |
| 6,503,521 B1 | 1/2003 | Atis | |
| 6,790,814 B1 | 9/2004 | Marin | |
| 6,802,295 B2 | 10/2004 | Fox | |
| 6,808,375 B2 | 10/2004 | Klotzer | |
| 6,825,161 B2 | 11/2004 | Shefer et al. | |
| 6,831,046 B2 * | 12/2004 | Carew et al. | 510/120 |
| 6,846,784 B2 | 1/2005 | Engel | |
| 6,943,200 B1 | 9/2005 | Corrand | |
| 7,015,181 B2 | 3/2006 | Lambino | |
| 7,285,520 B2 | 10/2007 | Krzysik | |
| 7,387,787 B2 | 6/2008 | Fox | |
| 7,846,462 B2 | 12/2010 | Spadini et al. | |
| 7,901,696 B2 | 3/2011 | Eknoian | |
| 2002/0064510 A1 | 5/2002 | Dalrymple | |
| 2002/0077264 A1 | 6/2002 | Roberts | |
| 2002/0081930 A1 | 6/2002 | Jackson | |
| 2002/0098994 A1 | 7/2002 | Zafar | |
| 2002/0099109 A1 | 7/2002 | Dufton | |
| 2002/0177621 A1 | 11/2002 | Hanada | |
| 2002/0187181 A1 | 12/2002 | Godbey | |
| 2003/0008790 A1 * | 1/2003 | Carew et al. | 510/119 |
| 2003/0032573 A1 | 2/2003 | Tanner | |
| 2003/0045441 A1 | 3/2003 | Hsu | |
| 2003/0069154 A1 | 4/2003 | Hsu | |
| 2003/0080150 A1 | 5/2003 | Cowan | |
| 2003/0099691 A1 | 5/2003 | Lydzinski | |
| 2003/0099692 A1 | 5/2003 | Lydzinski | |
| 2003/0180242 A1 | 9/2003 | Eccard | |
| 2003/0186826 A1 | 10/2003 | Eccard | |
| 2003/0194416 A1 | 10/2003 | Shefer | |
| 2003/0199412 A1 | 10/2003 | Gupta | |
| 2003/0207776 A1 | 11/2003 | Shefer | |
| 2003/0215522 A1 | 11/2003 | Johnson | |
| 2003/0232183 A1 | 12/2003 | Dufton | |
| 2004/0029762 A1 | 2/2004 | Hensley | |
| 2004/0032859 A1 | 2/2004 | Mino | |
| 2004/0048759 A1 | 3/2004 | Ribble | |
| 2004/0053808 A1 | 3/2004 | Raehse | |
| 2004/0071742 A1 | 4/2004 | Popplewell | |
| 2004/0071755 A1 | 4/2004 | Fox | |
| 2004/0108615 A1 | 6/2004 | Foley | |
| 2004/0110656 A1 | 6/2004 | Casey | |
| 2004/0126585 A1 | 7/2004 | Kerins | |
| 2004/0175404 A1 | 9/2004 | Shefer | |
| 2004/0202632 A1 | 10/2004 | Gott | |
| 2004/0206270 A1 | 10/2004 | Vanmaele | |
| 2004/0242772 A1 | 12/2004 | Huth | |
| 2005/0069575 A1 | 3/2005 | Fox | |
| 2005/0136780 A1 | 6/2005 | Clark | |
| 2005/0137272 A1 | 6/2005 | Gaserod | |
| 2005/0202992 A1 | 9/2005 | Grandio Portabales | |
| 2005/0220745 A1 | 10/2005 | Lu | |
| 2005/0232954 A1 | 10/2005 | Yoshinari | |
| 2005/0272836 A1 | 12/2005 | Yaginuma | |
| 2005/0287106 A1 | 12/2005 | Legendre | |
| 2006/0002880 A1 | 1/2006 | Peffly | |
| 2006/0052263 A1 | 3/2006 | Roreger | |
| 2006/0159729 A1 * | 7/2006 | Helfman et al. | 424/443 |
| 2006/0228319 A1 | 10/2006 | Vona | |
| 2007/0028939 A1 | 2/2007 | Mareri | |
| 2007/0149435 A1 | 6/2007 | Koenig | |
| 2007/0225388 A1 | 9/2007 | Cooper et al. | |
| 2008/0035174 A1 | 2/2008 | Aubrun-Sonneville | |
| 2008/0083420 A1 * | 4/2008 | Glenn et al. | 132/208 |
| 2008/0090939 A1 | 4/2008 | Netravali | |
| 2008/0131695 A1 | 6/2008 | Aouad | |
| 2008/0138492 A1 | 6/2008 | Cingotti | |
| 2008/0152894 A1 | 6/2008 | Beihoffer | |
| 2008/0215023 A1 | 9/2008 | Scavone | |
| 2008/0293839 A1 | 11/2008 | Stobby | |
| 2009/0232873 A1 | 9/2009 | Glenn, Jr. | |
| 2009/0263342 A1 | 10/2009 | Glenn, Jr. | |
| 2010/0167971 A1 | 7/2010 | Glenn, Jr. | |
| 2010/0173817 A1 | 7/2010 | Glenn, Jr. | |
| 2010/0179083 A1 | 7/2010 | Glenn, Jr. | |
| 2010/0279905 A1 | 11/2010 | Glenn, Jr. | |
| 2010/0286011 A1 | 11/2010 | Glenn, Jr. | |
| 2010/0291165 A1 | 11/2010 | Glenn, Jr. | |
| 2010/0298188 A1 | 11/2010 | Glenn, Jr. | |
| 2011/0023240 A1 | 2/2011 | Fossum | |
| 2011/0027328 A1 | 2/2011 | Baig et al. | |
| 2011/0028373 A1 | 2/2011 | Fossum | |
| 2011/0028374 A1 | 2/2011 | Fossum | |
| 2011/0182956 A1 | 7/2011 | Glenn, Jr. | |
| 2011/0189246 A1 | 8/2011 | Glenn, Jr. | |
| 2011/0195098 A1 | 8/2011 | Glenn, Jr. | |
| 2012/0021026 A1 | 1/2012 | Glenn, Jr. | |

FOREIGN PATENT DOCUMENTS

| | | | |
|---|---|---|---|
| EP | 1160311 B1 | 12/2001 | |
| EP | 1217987 B1 | 12/2004 | |
| EP | 1958532 A2 * | 8/2008 | |
| EP | 2085434 A1 | 8/2009 | |
| FR | 2871685 A | 12/2005 | |
| FR | 2886845 A | 12/2006 | |
| GB | 2235204 A | 2/1991 | |
| GB | 2355008 A | 4/2001 | |
| JP | 58021608 A | 2/1983 | |
| JP | 58216109 A | 12/1983 | |
| JP | 62072609 A | 4/1987 | |
| JP | 62072610 A | 4/1987 | |
| JP | 1313418 A | 12/1989 | |
| JP | 5344873 A | 12/1993 | |
| JP | 6017083 A | 1/1994 | |
| JP | 7089852 A | 4/1995 | |
| JP | 8325133 A | 12/1996 | |
| JP | 10251371 A | 9/1998 | |
| JP | 2003073700 A | 3/2003 | |
| JP | 2003082397 A | 3/2003 | |
| JP | 2004345983 A | 12/2004 | |
| JP | 2005171063 A | 6/2005 | |
| JP | 2007197540 A | 8/2007 | |
| JP | 2007091954 A | 12/2007 | |
| KR | 20020003442 | 1/2002 | |
| WO | WO9514495 A1 | 6/1995 | |
| WO | WO 9731616 A1 * | 9/1997 | |
| WO | WO01/24770 A1 | 4/2001 | |
| WO | WO 2004/032859 A | 4/2004 | |
| WO | WO2004/041991 A1 | 5/2004 | |
| WO | WO2005/003423 A1 | 1/2005 | |
| WO | WO2007033598 A1 | 3/2007 | |
| WO | WO2007/093558 A2 | 8/2007 | |
| WO | WO2009019571 | 2/2009 | |

OTHER PUBLICATIONS

C. D. Vaughan. Solubility, Effects in Product, Package, Penetration and Preservation, Cosmetics and Toiletries, vol. 103, Oct. 1988.
*Encyclopedia of Polymer Science and Engineering*, vol. 15, 2d ed., pp. 204-308, John Wiley & Sons, Inc. (1989).
Anonymous: "P8136 Poly(vinyl alcohol)" Internet article, [Online] XP002538935 Retrieved from the Internet: URL:http://www.sigmaaldrich.com/catalog/ProductDetail.do?D7=0&N25=Search_Concat_PNO%7CBRAND_Key&N4=P8136%7CSIAL&N25=0&QS=0N&F=SPEC> [retrieved on Jul. 28, 2009].

* cited by examiner

Micro-CT 3-D Image
of Dissolvable Porous Shampoo Solid

Super-imposed Cross-Sectional SEM Images
of Top-Middle-Bottom Regions of Dissolvable Porous Shampoo Solid

POROUS, DISSOLVABLE SOLID SUBSTRATE AND A SURFACE RESIDENT COATING OF CATIONIC SURFACTANT CONDITIONER

CROSS REFERENCE TO RELATE APPLICATION

This application claims the benefit of U.S. Provisional Application Ser. No. 61/267,702 filed Dec. 8, 2009.

FIELD OF THE INVENTION

The present invention relates to hair care compositions, especially those hair care compositions providing conditioning benefits in the form of an article comprising a porous dissolvable solid substrate and a cationic surfactant conditioner active.

BACKGROUND OF THE INVENTION

Hair care compositions have traditionally been sold as liquid products. These liquid hair care products typically comprise a substantial amount of water in the formula. In addition to being liquids, many of the hair care products contain conditioning agents to provide one or more consumer recognized benefits relating to shine, softness, combability, antistatic properties, wet-handling, and manageability. One of the most effective classes of hair conditioning agents are cationic surfactant conditioners which are prevalent within a wide variety of retail hair conditioner products.

Cationic surfactant conditioners can be difficult to formulate within liquid conditioning compositions due to the strong interactions that they can have with other ingredients. While such negative interactions are widely appreciated in compositions comprising anionic ingredients (e.g., anionic surfactants, anionic polymers etc.), the incorporation of cationic surfactant conditioners is also known to present formulation challenges in combinations with other ingredients, especially non-ionic fatty alcohol conditioners which are typically employed within hair conditioning products. In particular, the cationic surfactant conditioner must synergize with the fatty alcohols (and other co-surfactants) to produce an optimum lamellar gel network structure that delivers consumer acceptable product rheology and is shelf stable. The lamellar gel network must also deliver sufficient deposition of the cationic surfactant conditioner to deliver the intended primary conditioning benefit to the hair. Additionally, the degree gel network formation is strongly tied to the level of the cationic surfactant conditioner within the composition and in particular driven by the ratio of the cationic surfactant conditioner to the fatty alcohol. Moreover, the deposition of the cationic surfactant conditioner and the resulting degree of hair conditioning delivered is strongly driven by the level of the cationic surfactant conditioner within the lamellar gel network composition.

Hence, a trichotomy presently exists during the formulation of liquid hair conditioners comprising cationic surfactant conditioners toward achieving the simultaneous benefits of improved hair conditioning, consumer acceptable rheology, and product shelf stability. All three of these consumer objectives are directly and simultaneously driven by the level of the cationic surfactant conditioner within the composition (and it's ratios to other components) and the optimum levels required to deliver one objective may differ from the optimum levels required to deliver one or both of the other objectives. Moreover, this problem is compounded by the fact that there exist multiple consumer segments, each requiring different levels of hair conditioning and correspondingly different levels of cationic surfactant conditioner. This results in time consuming iterative and highly resource intensive formulation efforts.

Therefore, it is an object of the invention to provide a hair care product comprising cationic surfactant conditioners that offers greater formulation ease and flexibility. In particular, it is an object of the invention to provide a hair care product incorporating a cationic surfactant conditioner in such a way that the level of the cationic surfactant conditioner drives primarily or singly the original desired hair conditioning performance benefit and does not simultaneously drive other competing product benefits such as product rheology/appearance or product shelf stability.

Additionally, it is an object of the present invention to provide a method for processing a porous dissolvable solid substrate comprising a cationic surfactant conditioner, whereby said process allows for late stage differentiation. The cationic surfactant conditioner active can be added and modified without changing the basic formula of the hair conditioning composition. It is further an object of the present invention to provide a porous dissolvable solid substrate with a cationic surfactant conditioner in the form of a unit dose hair care product.

Additionally, it is an object of the present invention to provide a porous dissolvable solid substrate that can be conveniently and quickly dissolved in the palm of the consumer's hand to constitute a liquid hair care composition. Additionally, it is an object of the present invention to provide a porous dissolvable solid substrate that contains a cationic conditioner active and additional actives.

SUMMARY OF THE INVENTION

The present invention meets the aforementioned needs. The present invention provides a porous dissolvable solid substrate in the form of a unit dose hair care article that can be conveniently and quickly dissolved in the palm of the consumer's hand to reconstitute a liquid hair care composition for ease of application to hair while providing the consumer desired levels of both anionic cleansing surfactants and a cationic surfactant conditioner in a form that can be more easily and flexibly formulated.

The present invention provides a hair care article comprising (1) a porous dissolvable solid substrate comprising from about 10% to about 75% of a surfactant, from about 10% to about 50% water-soluble polymer, from about 1% to about 30% plasticizer; and (2) a surface resident coating comprising from about 10% to about 100% of one or more cationic surfactant conditioner actives; wherein the ratio of the porous dissolvable solid substrate to the surface resident coating is from about 110:1 to about 0.5:1.

In another aspect, the present invention provides a method for making the hair care article, comprising: (1) preparing a processing mixture comprising from about 5% to about 50% of a surfactant(s), from about 5% to about 35% water-soluble polymer, and from about 0.5% to about 20% plasticizer; (2) aerating the processing mixture by introducing a gas into the processing mixture to form an aerated wet mixture; (3) forming the aerated wet mixture into one or more desired shapes; (4) drying the aerated wet mixture to form a porous dissolvable solid substrate; and (5) applying a surface resident coating of the cationic surfactant conditioner active in powdered form to the porous dissolvable solid substrate.

BRIEF DESCRIPTION OF THE DRAWINGS

While the specification concludes with claims which particularly point out and distinctly claim the present invention, it is believed that the present invention will be better understood from the following description of embodiments, taken in conjunction with the accompanying drawings, in which like reference numerals identify identical elements and wherein:

DETAILED DESCRIPTION OF THE INVENTION

Figure 1:
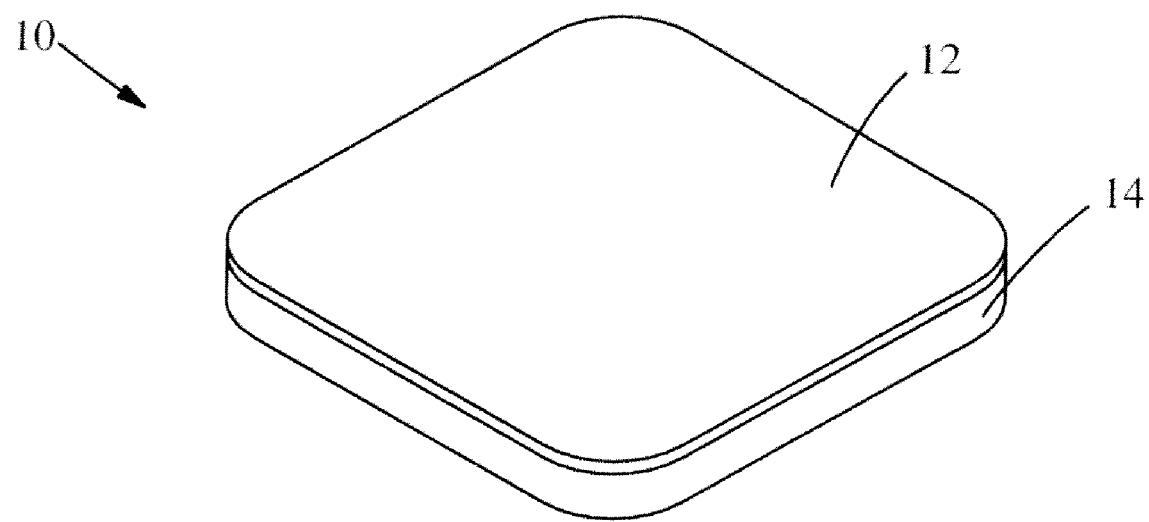
FIG. 1 is a schematic view of a porous dissolvable solid substrate with a surface resident cationic surfactant conditioner active.

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

I. Definitions

As used herein, the term "hair care composition" means a composition that may be applied to mammalian hair and skin without undue undesirable effects.

As used herein, the term "conditioning benefits" refers to one or more consumer recognized benefits relating to shine, softness, combability, antistatic properties, wet-handling, damage, manageability, body, and greasiness delivered by isolated cationic conditioning actives.

As used herein, the term "cationic surfactant conditioning active" means one or a mixture of more than one material(s) selected from the group consisting of alkyl quaternary ammonium salts and alkyl amines. The amines include those which are cationic at pH 7, and in one embodiment are also in salt form.

The term, "surface resident coating comprising a cationic surfactant conditioner active," as used herein, refers to a particulate solid composition or material comprising at least one cationic surfactant conditioning active that is adsorbed to at least a portion of the solid/air interface of the porous dissolvable solid substrate. The resulting surface resident coating minimizes the physical interactions between the incorporated cationic surfactant conditioner and the anionic surfactants present within the bulk of the dissolvable porous solid over the shelf life of the product, and before the hair care article is put in contact with water during consumer use.

As used herein, "hair care article" means the porous dissolvable solid substrate comprising an anionic surfactant, water-soluble polymer, and plasticizer, and the surface resident coating comprising a cationic surfactant conditioner active. The hair care article may be referred to herein as "the article."

As used herein, "dissolvable" means that the porous dissolvable solid substrate has a dissolution rate that satisfies the Hand Dissolution Method Test described herein.

As used herein "porous dissolvable solid substrate" means a solid polymer-containing matrix that defines an interconnected network of spaces or cells that contain the gas of the surrounding atmosphere, typically air. The interconnectivity of the structure may be described by a Star Volume, a Structure Model Index (SMI) or a Percent Open Cell Content.

II. Hair Care Article

The present invention provides a porous dissolvable solid substrate in the form of a unit dose hair care article that can be conveniently and quickly dissolved in the palm of the consumer's hand to reconstitute a liquid hair care composition for ease of application to hair while providing the consumer desired levels of a cationic surfactant conditioner in a form that can be more easily and flexibly formulated.

This is achieved by incorporating the cationic surfactant conditioner active as a surface resident coating on the porous dissolvable solid substrate rather than adding the cationic surfactant conditioner active to the continuous solid structure of the porous dissolvable solid substrate during the making process. Any suitable application method can be used to apply the cationic surfactant conditioner active to the porous dissolvable solid substrate to form a surface resident coating that is adsorbed to at least a portion of the solid/air interface of the porous dissolvable solid substrate. In a preferred embodiment the cationic conditioner active is a powder coating, which is applied to the surface of the porous dissolvable solid substrate. Traditionally, cationic surfactant conditioner actives (i.e., alkyl quaternary ammonium salts and alkyl amine salts) are formulated within aqueous liquid hair conditioner compositions in such a way where they can directly interact with other actives (i.e., fatty alcohols, other surfactants etc.) and thereby influence multiple product performance attributes in addition to the desired hair conditioning performance. This is especially problematic in the formulation of hair conditioner products wherein the cationic surfactant conditioner must synergize with the fatty alcohols (and other co-surfactants) to produce an optimum lamellar gel network structure that must also deliver consumer acceptable product rheology and meet shelf stability requirements. This creates a trichotomy as differing levels of the cationic surfactant conditioner (and differing ratios with the fatty alcohols and other actives) may be required of the cationic surfactant conditioner within the lamellar gel network composition to deliver each of the three desired benefits. This problem is exacerbated by the fact that differing hair conditioner product versions, each with it's own target conditioning level and corresponding level of cationic surfactant conditioner, are typically required across a given branded product line to appeal to the differing consumer segments. Correspondingly, there exist significant formulation complexities during the formulation of liquid hair conditioning products requiring time consuming and resource intensive formulation efforts and inevitable performance trade-offs.

The present invention alleviates these formulation complexities and trade-offs by providing porous dissolvable solid substrate in the form of a unit dose hair care article that can be conveniently and quickly dissolved in the palm of the consumer's hand to reconstitute a liquid hair care composition for ease of application to hair while providing the consumer desired levels of a cationic surfactant conditioner in the form of a surface resident coating that can be more easily and flexibly formulated.

A. The Porous Dissolvable Solid Substrate

The porous dissolvable solid substrate comprises an anionic surfactant, a water-soluble polymer, and a plasticizer. The porous dissolvable solid substrate can be prepared such that it can be conveniently and quickly dissolved in the palm of the consumer resulting in a liquid hair care composition. Once dissolved, this hair care composition can be used in a manner similar to a conventional liquid hair care compositions, i.e. applied to the scalp and/or hair. It has been found that such porous dissolvable solid substrate can now deliver performance similar to that of today's liquid hair care compositions. The porous dissolvable solid substrate has a maximum Cell Wall Thickness. The porous dissolvable solid substrate has a Cell Wall Thickness of from about from about 0.02 mm to about 0.15 mm, in one embodiment from about 0.025 mm to about 0.12 mm, in another embodiment from about 0.03 mm to about 0.09 mm, and in still another embodiment from about 0.035 mm to about 0.06 mm. The porous dissolvable solid substrate has a minimum level of interconnectivity between the cells, which is quantified by the Star Volume, the Structure Model Index (SMI), and the Percent Open Cell Content. The porous dissolvable solid substrate has a Star Volume of from about 1 $mm^3$ to about 90 $mm^3$, in one embodiment from about 1.5 $mm^3$ to about 60 $mm^3$, in another embodiment from about 2 $mm^3$ to about 30 $mm^3$, and in still another embodiment from about 2.5 $mm^3$ to about 15 $mm^3$. The porous dissolvable solid substrate has a non-negative Structure Model Index of from about 0.0 to about 3.0, in one embodiment from about 0.5 to about 2.75, and in another embodiment from about 1.0 to about 2.50. The porous dissolvable solid substrate has a Percent Open Cell Content of from about 80% to 100%, in one embodiment from about 85% to about 97.5%, and in another embodiment from about 90% to about 95%. The porous dissolvable solid substrate also has a minimum Specific Surface Area. The porous dissolvable solid substrate has a Specific Surface Area of from about 0.03 $m^2/g$ to about 0.25 $m^2/g$, in one embodiment from about 0.035 $m^2/g$ to about 0.22 $m^2/g$, in another embodiment from about 0.04 $m^2/g$ to about 0.19 $m^2/g$, and in still another embodiment from about 0.045 $m^2/g$ to about 0.16 $m^2/g$. The porous dissolvable solid substrate has a basis weight of from about 125 grams/$m^2$ to about 3,000 grams/$m^2$, in one embodiment from about 300 grams/$m^2$ to about 2,500 grams/$m^2$, in another embodiment from about 400 grams/$m^2$ to about 2,000 grams/$m^2$, in another embodiment from about 500 grams/$m^2$ to about 1,500 grams/$m^2$ and in another embodiment from about 600 grams/$m^2$ to about 1,200 grams/$m^2$, and in another embodiment from about 700 to about 1,000 grams/$m^2$ The porous dissolvable solid substrate has a solid density of from about 0.03 $g/cm^3$ to about 0.40 $g/cm^3$, in one embodiment from about 0.05 $g/cm^3$ to about 0.35 $g/cm^3$, in another embodiment from about 0.08 $g/cm^3$ to about 0.30 $g/cm^3$, in another embodiment from about 0.10 $g/cm^3$ to about 0.25 $g/cm^3$, and in another embodiment from about 0.12 $g/cm^3$ to about 0.20 $g/cm^3$.

In one embodiment, the porous dissolvable solid substrate of present invention is a flat, flexible substrate in the form of a pad, a strip or tape and having a thickness of from about 0.5 mm to about 10 mm, in one embodiment from about 1 mm to about 9 mm, in another embodiment from about 2 mm to about 8 mm, and in a further embodiment from about 3 mm to about 7 mm as measured by the below methodology. In another embodiment, the porous dissolvable solid substrate of the present invention can also take the form of a dissolvable fibrous web structure.

1. Surfactants

The porous dissolvable solid substrates of the present invention may be non-lathering under consumer relevant usage instructions. The porous dissolvable substrates include at least one surfactant as a processing aid to generate a stable foam solid prior to drying (solidification).

The non-lathering porous dissolvable solid substrates comprise from about 10% to about 75%, in another embodiment from about 15% to about 60%, and in another embodiment from about 20% to about 50% by weight of the hair care article of surfactant; wherein the surfactant comprises one or more of the surfactants described below.

(i) Anionic Surfactants

The hair care products of the present invention are non-lathering, and therefore may comprise a maximum level of 10% (or less than 10%) of anionic surfactants to be used primarily as a process aid in making a stable foam solid. Additional, non-ionic surfactants can be combined with the anionic surfactants to reach a surfactant level which generates a stable foam solid prior to drying.

(ii) Cationic Surfactants

In one embodiment cationic surfactants are included as a process aid in making a stable porous dissolvable solid substrate. Suitable cationic surfactants for use in the present invention include those described in McCutcheon's Detergents and Emulsifiers, North American edition (1986), Allured Publishing Corp., and McCutcheon's Functional Materials, North American edition (1992). Suitable quaternary ammonium cationic conditioner actives can include cetyltrimethylammonium chloride, behenyltrimethylammonium chloride (BTAC), stearyltrimethylammonium chloride, cetylpyridinium chloride, octadecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, distearyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by halogen, (e.g., bromide), acetate, citrate, lactate, glycolate, phosphate nitrate, sulphate, or alkylsulphate.

In a particular embodiment, the quaternary ammonium cationic conditioner actives for use in the invention are cetyltrimethylammonium chloride, available commercially, for example as GENAMIN CTAC by Clariant and Arquad 16/29 supplied by Akzo Nobel, behenyltrimethylammonium chloride (BTMAC) such as GENAMIN KDMP supplied by Clariant, and distearyldimethylammonium chloride such as GENAMIN DSAP supplied by Clariant. Mixtures of any of the foregoing materials may also be suitable. In a preferred embodiment, the quaternary ammonium cationic conditioner active is behenyltrimethylammonium chloride (BTMAC).

(iii) Non-Ionic Surfactants

In one embodiment non-ionic surfactants are included as a process aid in making a stable porous dissolvable solid substrate. Suitable nonionic surfactants for use in the present invention include those described in McCutcheon's Detergents and Emulsifiers, North American edition (1986), Allured Publishing Corp., and McCutcheon's Functional Materials, North American edition (1992). Suitable nonionic surfactants for use in the hair care compositions of the present invention include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

(iv) Polymeric Surfactants

Polymeric surfactants can also be surfactants to be employed as a process aid in making the porous dissolvable solid substrate of the present invention, either alone or in combination with ionic and/or nonionic surfactants. Suitable polymeric surfactants for use in the hair care compositions of the present invention include, but are not limited to, block copolymers of ethylene oxide and fatty alkyl residues, block copolymers of ethylene oxide and propylene oxide, hydrophobically modified polyacrylates, hydrophobically modified celluloses, silicone polyethers, silicone copolyol esters, diquaternary polydimethylsiloxanes, and co-modified amino/polyether silicones.

2. Water-Soluble Polymer ("Polymer Structurant")

The porous dissolvable solid substrate comprises water-soluble polymers that function as a structurant. As used herein, the term "water-soluble polymer" is broad enough to include both water-soluble and water-dispersible polymers, and is defined as a polymer with a solubility in water, measured at 25° C., of at least about 0.1 gram/liter (g/L). In some embodiments, the polymers have solubility in water, measured at 25° C., of from about 0.1 gram/liter (g/L). to about 500 grams/liter (g/L). (This indicates production of a macroscopically isotropic or transparent, colored or colorless solution). The polymers for making these solids may be of synthetic or natural origin and may be modified by means of chemical reactions. They may or may not be film-forming. These polymers should be physiologically acceptable, i.e., they should be compatible with the skin, mucous membranes, the hair and the scalp.

The water-soluble polymer may be present from about 10% to about 50% by weight of the porous dissolvable solid substrate of one or more water-soluble polymer, in one embodiment from about 15% to about 40%, and in a particular embodiment from about 20% to about 30% by weight of the porous dissolvable solid substrate of one or more water-soluble polymers.

The one or more water-soluble polymers of the present invention are selected such that their weighted average molecular weight is from about 40,000 to about 500,000, in one embodiment from about 50,000 to about 400,000, in yet another embodiment from about 60,000 to about 300,000, and in still another embodiment from about 70,000 to about 200,000. The weighted average molecular weight is computed by summing the average molecular weights of each polymer raw material multiplied by their respective relative weight percentages by weight of the total weight of polymers present within the porous solid.

In one embodiment, at least one of the one or more water-soluble polymers is chosen such that about 2% by weight solution of the water-soluble polymer gives a viscosity at 20° C. of from about 4 centipoise to about 80 centipoise; in an alternate embodiment from about 5 centipoise to about 70 centipoise; and in another embodiment from about 6 centipoise to about 60 centipoise.

The water-soluble polymer(s) of the present invention can include, but are not limited to, synthetic polymers as described in U.S. Ser. No. 61/120,786 including polymers derived from acrylic monomers such as the ethylenically unsaturated carboxylic monomers and ethylenically unsaturated monomers as described in U.S. Pat. No. 5,582,786 and EP-A-397410. The water-soluble polymer(s) which are suitable may also be selected from naturally sourced polymers including those of plant origin examples which are described in U.S. Ser. No. 61/120,786. Modified natural polymers are also useful as water-soluble polymer(s) in the present invention and are included in U.S. Ser. No. 61/120,786. In one embodiment, water-soluble polymers of the present invention include polyvinyl alcohols, polyacrylates, polymethacrylates, copolymers of acrylic acid and methyl acrylate, polyvinylpyrrolidones, polyalkylene oxides, starch and starch derivatives, pullulan, gelatin, hydroxypropylmethylcelluloses, methycelluloses, and carboxymethycelluloses. In another embodiment, water-soluble polymers of the present invention include polyvinyl alcohols, and hydroxypropylmethylcelluloses. Suitable polyvinyl alcohols include those available from Celanese Corporation (Dallas, Tex.) under the CELVOL® trade name. Suitable hydroxypropylmethylcelluloses include those available from the Dow Chemical Company (Midland, Mich.) under the METHOCEL® trade name including combinations with above mentioned hydroxypropylmethylcelluloses.

In a particular embodiment, the above mentioned water-soluble polymer(s) may be blended with any single starch or combination of starches as a filler material in such an amount as to reduce the overall level of water-soluble polymers required, so long as it helps provide the hair care article with the requisite structure and physical/chemical characteristics as described herein.

In such instances, the combined weight percentage of the water-soluble polymer(s) and starch-based material generally ranges from about 10% to about 50%, in one embodiment from about 15% to about 40%, and in a particular embodiment from about 20% to about 30% by weight relative to the total weight of the porous dissolvable solid substrate. The weight ratio of the water-soluble polymer(s) to the starch-based material can generally range from about 1:10 to about 10:1, in one embodiment from about 1:8 to about 8:1, in still another embodiment from about 1:7 to about 7:1, and in yet another embodiment from about 6:1 to about 1:6.

Typical sources for starch-based materials can include cereals, tubers, roots, legumes and fruits. Native sources can include corn, pea, potato, banana, barley, wheat, rice, sago, amaranth, tapioca, arrowroot, canna, sorghum, and waxy or high amylase varieties thereof. The starch-based materials may also include native starches that are modified using any modification known in the art, including those described in U.S. Ser. No. 61/120,786.

3. Plasticizer

The porous dissolvable solid substrate of the present invention comprises a water soluble plasticizing agent suitable for use in hair care compositions. In one embodiment, the one or more plasticizers may be present from about 1% to about 30% by weight of the porous dissolvable solid substrate; in another embodiment from about 3% to about 25%; in another embodiment from about 5% to about 20%, and in yet another embodiment, from about 8% to about 15%. Non-limiting examples of suitable plasticizing agents include polyols, copyols, polycarboxylic acids, polyesters and dimethicone copyols. Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, and high fructose corn syrup solids and ascorbic acid. Suitable examples of polycarboxylic acids for use herein are disclosed in U.S. Ser. No. 61/120,786.

In one embodiment, the plasticizers include glycerin or propylene glycol and combinations thereof. European Patent Number EP283165B1 discloses other suitable plasticizers, including glycerol derivatives such as propoxylated glycerol.

4. Optional Ingredients

The porous dissolvable solid substrate may further comprise other optional ingredients that are known for use or otherwise useful in hair care compositions, provided that such optional materials are compatible with the selected essential materials described herein, or do not otherwise unduly impair the performance of the hair care composition.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. Examples of such optional ingredients are disclosed in U.S. Ser. No. 12/361,634. Additional optional ingredients include anti-dandruff actives including but not limited to zinc pyrithione, selenium sulfide and those actives disclosed in US Publication 2003/0215522A1.

Other optional ingredients include organic solvents, especially water miscible solvents and co-solvents useful as solublizing agents for polymeric structurants and as drying accelerators Examples of suitable organic solvents are disclosed in U.S. Ser. No. 12/361,634. Other optional ingredients include: latex or emulsion polymers, thickeners such as water soluble polymers, clays, silicas, ethylene glycol distearate, deposition aids, including coacervate forming components.

In addition to the anionic surfactants, other non-anionic surfactants may be included. These non-anionic surfactants may include nonionic surfactants, cationic surfactants, zwitterionic surfactants, amphoteric surfactants, or combinations thereof. Examples of these non-anionic surfactants can be found in U.S. Ser. No. 61/120,786.

B. Surface Resident Coating comprising a Cationic Surfactant Conditioner Active

In one embodiment, the porous dissolvable solid substrates provide a continuous and accessible high surface area "scaffold" (a 3-D network of "struts") for the surface resident coating comprising the cationic surfactant conditioner active to be adsorbed or distributed across, creating a high surface area thin coating.

In one embodiment the surface resident coating comprises from about 10% to about 100% of one or more cationic surfactant conditioner actives; in another embodiment from about 25% to about 100%, and in yet another embodiment from about 40% to about 100%. In one embodiment the ratio of the porous dissolvable solid substrate to the surface resident coating comprising the cationic surfactant conditioner active is from about 110:1 to about 0.5:1, in another embodiment from about 20:1 to about 1:1, in another embodiment from about 10:1 to about 1.5:1, and in yet another embodiment from about 7:1 to about 3:1.

Suitable cationic surfactant conditioner actives for use in compositions of the invention contain amino or quaternary ammonium hydrophilic moieties which are positively charged when dissolved in the composition.

Suitable quaternary ammonium cationic conditioner actives useful herein include, but are not limited to, those having the formula (I):

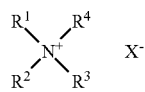

in which $R^1$, $R^2$, $R^3$, and $R^4$ are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate, nitrate, sulphate, and alkylsulphate radicals. In one embodiment, the alkylsulphate radical is methosulfate and/or ethosulfate.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated and branched or unbranched. In one embodiment, the class of cationic conditioner actives of general formula (I), $R^1$ and $R^2$ are each independently selected from $C_{16}$ to $C_{22}$ hydrocarbyl chains comprising at least one ester linkage in both $R^1$ and $R^2$, and $R^3$ and $R^4$ are each independently selected from $CH_3$ and $CH_2CH_2OH$. In another embodiment, the class of cationic conditioner actives of general formula (I), $R^1$ and $R^2$ are each independently selected from $C_{16}$ to $C_{22}$ saturated or unsaturated, and $R^3$ and $R^4$ are each independently selected from $CH_3$, $CH_2CH_2OH$, and $CH_3$. In yet another embodiment, the class of cationic conditioner actives of general formula (I), $R^1$ is a $C_{16}$ to $C_{22}$ alkyl chain and $R^2$, $R^3$ and $R^4$ are each independently selected from $CH_3$, CH2CHOH, and $CH_3$.

Suitable quaternary ammonium cationic conditioner actives of general formula (I) can include cetyltrimethylammonium chloride, behenyltrimethylammonium chloride (BTAC), stearyltrimethylammonium chloride, cetylpyridinium chloride, octadecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, distearyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by halogen, (e.g., bromide), acetate, citrate, lactate, glycolate, phosphate nitrate, sulphate, or alkylsulphate.

In a particular embodiment, the quaternary ammonium cationic conditioner actives for use in the invention are cetyltrimethylammonium chloride, available commercially, for example as GENAMIN CTAC by Clariant and Arquad 16/29 supplied by Akzo Nobel, behenyltrimethylammonium chloride (BTMAC) such as GENAMIN KDMP supplied by Clariant, and distearyldimethylammonium chloride such as GENAMIN DSAP supplied by Clariant. Mixtures of any of the foregoing materials may also be suitable. In a preferred embodiment, the quaternary ammonium cationic conditioner active is behenyltrimethylammonium chloride (BTMAC).

Other suitable cationic surfactant conditioner actives can include salts of primary, secondary, and tertiary fatty amines. In one embodiment, the alkyl groups of such amines have from about 12 to about 22 carbon atoms, and can be substituted or unsubstituted. These amines are typically used in combination with an acid to provide the cationic species.

Suitable alkyl amine salts useful herein include, but are not limited to, those salts corresponding to alkyl amines having the general formula (II):

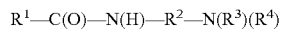

$$R^1-C(O)-N(H)-R^2-N(R^3)(R^4)$$

in which $R^1$ is a fatty acid chain containing from 12 to 22 carbon atoms, $R^2$ is an alkylene group containing from one to four carbon atoms, and $R^3$ and $R^4$ are, independently, an alkyl group having from one to four carbon atoms. $R^1$ can be saturated or unsaturated and branched or unbranched.

Suitable materials of general formula (II) are stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and diethylaminoethylstearamide.

Other suitable alkyl amine salts can include dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidyl behenylamine. In a preferred embodiment, the alkyl amine salt is stearamidopropyldimethylamine. Mixtures of any of the foregoing materials may also be suitable.

The acid used to provide the cationic conditioner active can be any organic acid or mineral acid of sufficient acid strength to neutralize a free amine nitrogen. Such acids include hydrochloric acid, sulphuric acid, nitric acid, phosphoric acid, lactic acid, citric acid, tartaric acid, acetic acid, gluconic acid, glycolic acid and propionic acid, or combinations thereof. In one embodiment, a sufficient amount of acid is added to neutralize the amidoamine compound and to adjust the final pH of the composition to within a range of from about 2.5 to about 6; in another embodiment, from about 3 to about 5. In one embodiment, the molar ratio of protonatable amine groups to $H^+$ from the acid is from about 1:0.3 to about 1:1.2; and in another embodiment, from about 1:0.5 to about 1:1.1. Mixtures of any of the above-described cationic conditioner actives may also be suitable.

The surface resident coating comprising the cationic surfactant conditioner is applied to the porous dissolvable solid substrate in particulate form. In one embodiment, the surface resident coating comprising the cationic surfactant conditioner active is in the form of a fine powder. As seen in FIG. 1, in certain embodiments of the present invention, the hair care article 10 contains a surface resident coating comprising a cationic surfactant conditioner active 12 that is located on at least a portion of the surface of the porous dissolvable solid substrate 14. It will be appreciated that the isolated surface resident coating comprising the cationic surfactant conditioner active 12 may not always be adjacent to the porous dissolvable solid substrate 14. In certain embodiments, the surface resident coating comprising the cationic surfactant conditioner active 12 may permeate the porous dissolvable solid substrate 14 in whole or in part.

Figure 3A:
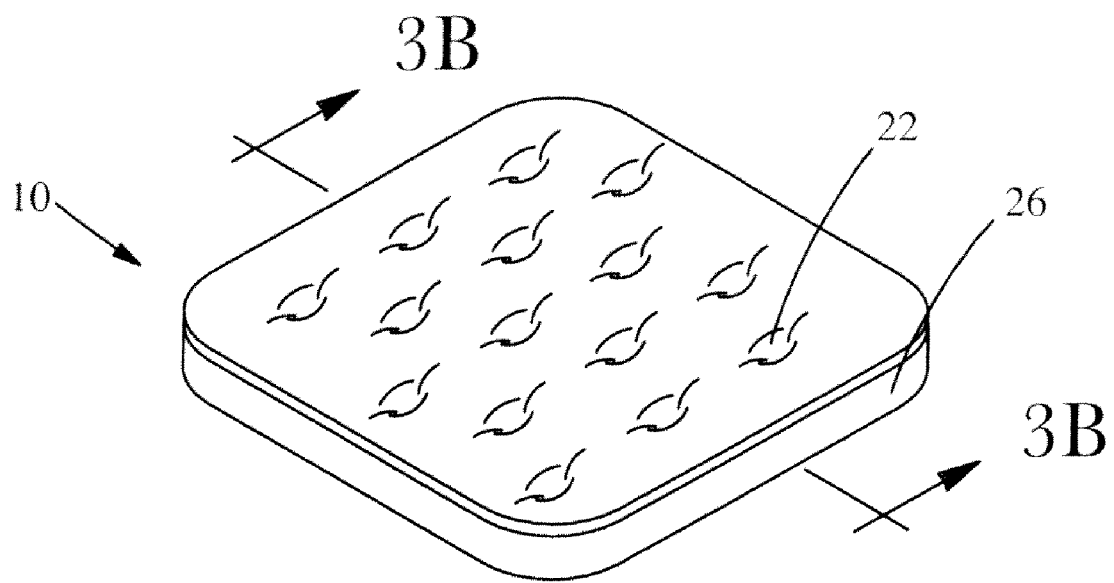
FIGS. 3A and 3B are a schematic view of a dimpled porous dissolvable solid substrate with a surface resident cationic surfactant conditioner active inside the dimples.
Figure 3B:
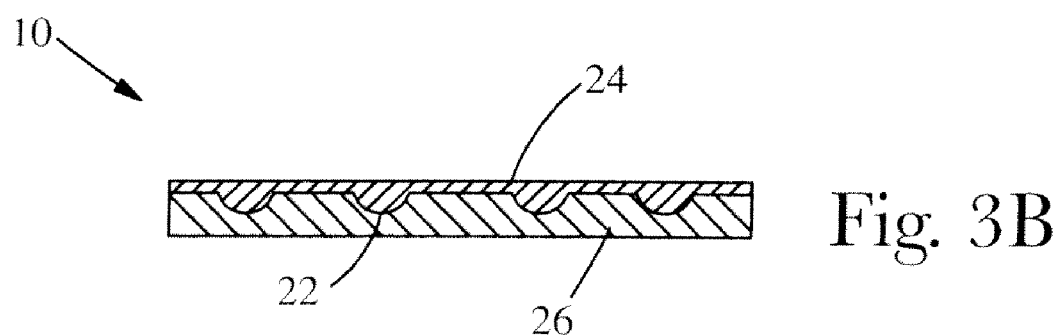

Alternatively, the surface resident coating comprising the cationic conditioner active can be included (e.g., sandwiched or encased) within the hair care article or parts thereof. Such a surface resident coating comprising the cationic surfactant conditioner active can be sprayed, dusted, sprinkled, coated, surface-printed (e.g., in the shape of a desired adornment, decoration, or pattern), poured on, injected into the interior, dipped, or by any other suitable means, such as by use of a depositor, sifter, or powder bed. In the embodiments depicted by FIGS. 3A, 3B, and 4, the hair care article 10 contains a surface resident coating comprising the cationic surfactant conditioner active that can be situated below the surface of the porous dissolvable solid substrate. As seen in FIG. 3B which is a cross sectional view of the hair care article 10, the surface resident coating comprising the cationic surfactant conditioner active 24 is located within the dimples 22 of the porous dissolvable solid substrate 26.

Figure 2:
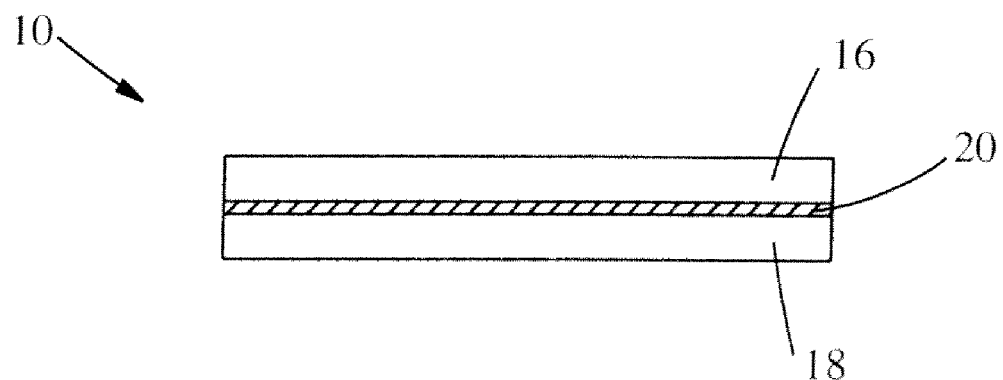
FIG. 2 is a schematic view of two porous dissolvable solid substrates with a surface resident cationic surfactant conditioner active layer in between the two substrates.

Referring now to FIG. 2, in certain embodiments the powder is sandwiched between two porous dissolvable solid substrate which are then joined together (e.g., via sealing the adjoining surfaces or edges with a thin layer of water and/or plasticizer so as to not substantially dissolve the porous dissolvable solid substrate and applied pressure to induce adhesion). In this embodiment, the hair care article 10 comprises two porous dissolvable solid substrates 16, 18 in between which a surface resident coating comprising the cationic surfactant conditioner active 20 is located.

Figure 4:
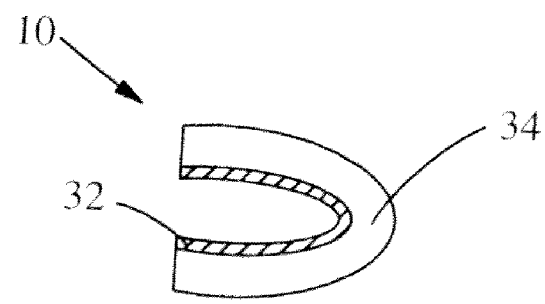
FIG. 4 is a schematic view of a porous dissolvable solid substrate that is folded over to enclose a surface resident cationic surfactant conditioner active.

Alternatively, in certain embodiments, the powder may be on one hair care article which is folded over to form a pouch, encasing the powder. As depicted in FIG. 4, the hair care article 10 comprises a surface resident coating comprising the cationic surfactant conditioner active 32 that is enclosed within a folded porous dissolvable solid substrate 34.

Due to the porous nature of the substrate, the surface resident coating comprising the cationic surfactant conditioning actives of the present invention generally does not spread uniformly across all exposed solid/air interfaces. Rather, the surface resident coatings of the present invention are typically distributed mostly across the outer surface layer of the porous dissolvable substrate from where it is applied and with some particulates distributing into cavities down to about 0.5 to 3 mm according to gravity and the coating process employed.

In addition to the cationic surfactant conditioner active, the surface resident coating can include additional excipients, for instance for the purposes of improving the flow properties of the powder during application or to serve as a carrier for the cationic surfactant conditioner active or as a filler material. Such excipients can include, but are not limited to, starches, modified starches, talc, silicas (silicon dioxide), silicates, calcium silicate, amorphous silicas, calcium carbonates, magnesium carbonates, sodium aluminosilicates, zinc carbonates, aluminum starch octenylsuccinates, and mixtures thereof. In a preferred embodiment, the filler material is an aluminum starch octenylsuccinate under the trade name DRY-FLO® PC and available from Akzo Nobel.

The surface resident coating comprising the cationic surfactant conditioner active can also include additional optional cosmetic actives including perfumes, silicones, cationic polymers, feel modifiers, etc. including any cosmetic active approved for use in cosmetics such as are described in reference books such as the CTFA Cosmetic Ingredient Handbook, Second Edition, The Cosmetic, Toiletries, and Fragrance Association, Inc. 1988, 1992. Examples of such optional ingredients are disclosed in U.S. Ser. No. 12/361, 634. The surface resident coating may also include optional cosmetic active particulate complexes including but not limited to starch perfume matrix microspheres, perfume loaded inorganic absorbent powders, beta cyclodextrin encapsulated perfumes, and combinations thereof. Additional optional actives include anti-dandruff actives including but not limited to zinc pyrithione, selenium sulfide and those actives disclosed in US Publication 2003/0215522A1.

It is also recognized that the surface resident cationic surfactant conditioner coatings of the present invention can be coated onto a porous dissolvable substrate that does not comprise an anionic surfactant for formulation advantages such as late stage differentiation, to improve product shelf stability, or to decrease formulation complexity etc. In these cases, the porous dissolvable substrate can be comprised of predominantly non-ionic or even cationic surfactants which may otherwise be physically compatible with the cationic surfactant conditioner active. Additionally the surface resident coating comprising the cationic surfactant conditioner active may be adsorbed to porous dissolvable substrates comprising other types of actives which have potential to negatively interact with the cationic surfactant conditioner active including but not limited to highly charged anionic polymers, anionic particles, anionic dispersions etc.

In one embodiment, the surface resident coating of the present invention may incorporate cationic actives other than cationic or surfactant conditioners including, but not limited to, cationic polymers or cationic dyes. Zwitterionic materials (surfactants, polymers, dyes etc.) are also suitable for incorporation within the surface resident coatings of the present invention.

Examples of the cationic polymers include cationized cellulose derivatives, cationic starch, cationized guar gum derivatives, homopolymer of diallyl quaternary ammonium salt, diallyl quaternary ammonium salt/acrylamide copolymer, quaternized polyvinyl-pyrrolidone derivatives, polyglycol polyamine condensation products, vinylimidazolium trichloride/vinylpyrrolidone copolymer, hydroxyethylcellulose/dimethyldiallylammonium chloride copolymer, vinylpyrrolidone/quaternized dimethylaminoethyl methacrylate copolymer, polyvinylpyrrolidone/alkyl aminoacrylate copolymer, polyvinylpyrrolidone/alkyl aminoacrylate/vinyl caprolactam copolymers, vinylpyrrolidone/methacrylamidopropyl trimethylammonium chloride copolymer, alkylacrylamide/acrylate/alkylaminoalkylacrylamide/polyethylene glycol methacrylate copolymers, adipic acid/dimethylaminohydroxypropyl ethylenetriamine copolymer, and cationic polymers disclosed in JP-A-53139734 and JP-A-60036407. Among these, preferred are cationized cellulose derivatives, cationized guar gum derivatives, and diallyl quaternary ammonium salt/acrylamide copolymers.

Cationic dyes may include those of the azo type, thiazole type, stilbene type, anthraquinone type, indigoid type, quinacridone type, quinophthalone type, aminoketone type, hydroxyketone type, phthalocyanine type, formazan type, cyanine type, nitro type, nitroso type, diphenylmethane type, triarylmethane type, xanthene type, acridine type, azine type, oxazine type, thiazine type, indamine type, indophenol type, and lactone types. Some examples include, but are not limited to, Basic Blue 6, Basic Blue 7, Basic Blue 9, Basic Blue 26, Basic Blue 41, Basic Blue 99, Basic Brown 4, Basic Brown 16, Basic Brown 17, Basic Green 1, Basic Red 2, Basic Red 22, Basic Red 76, Basic Violet 1, Basic Violet 3, Basic Violet 10, Basic Violet 14, Basic Yellow 11, and Basic Yellow 57 as are described in reference books such as the CTFA Cosmetic Ingredient Handbook, Second Edition, The Cosmetic, Toiletries, and Fragrance Association, Inc. 1988, 1992.

III. Product Form of the Hair Care Article

The hair care article can be produced in any of a variety of product forms, including porous dissolvable solid substrates along with the surface resident coating comprising the cationic surfactant conditioner active used alone or in combination with other hair care components. Regardless of the product form, the product form embodiments contemplated herein include the selected and defined hair care article that comprises a combination of a porous dissolvable solid substrate and a surface resident coating comprising a cationic surfactant conditioner active.

In one embodiment, the hair care article is in the form of one or more flat sheets or pads of an adequate size to be able to be handled easily by the user. It may have a square, rectangle or disc shape or any other suitable shape. The hair care articles can also be in the form of a continuous strip including delivered on a tape-like roll dispenser with individual portions dispensed via perforations and or a cutting mechanism. Alternatively, the hair care articles are in the form of one or more cylindrical objects, spherical objects, tubular objects or any other shaped object.

The hair care article may comprise one or more textured, dimpled or otherwise topographically patterned surfaces including letters, logos or figures. The textured substrate can result from the shape of the substrate, in that the outermost surface of the substrate contains portions that are raised with respect to other areas of the surface. The raised portions can result from the formed shape of the hair care article, for example the hair care article can be formed originally in a dimpled or waffle pattern. The raised portions can also be the result of creping processes, imprinted coatings, embossing patterns, laminating to other layers having raised portions, or the result of the physical form of the porous dissolvable solid substrate itself. The texturing can also be the result of laminating one porous dissolvable solid substrate to a second porous dissolvable solid substrate that is textured. In a particular embodiment, the hair care article can be perforated with holes or channels penetrating into or through the porous solid.

IV. Method of Manufacture

The hair care article can be prepared by the process comprising: (1) Preparing a processing mixture comprising anionic surfactant(s), dissolved polymer structurant, and plasticizer; (2) Aerating the processing mixture by introducing a gas into the processing mixture to form an aerated wet mixture; (3) Forming the aerated wet mixture into one or more desired shapes; (4) Drying the aerated wet mixture to form a porous dissolvable solid substrate; and (5) Applying the surface resident coating comprising a cationic surfactant conditioner active in powdered form to the porous dissolvable solid substrate.

A. Preparation of Processing Mixture

The processing mixture is generally prepared by dissolving the polymer structurant in the presence of water, plasticizer and other optional ingredients by heating followed by cooling. This can be accomplished by any suitable heated batch agitation system or via any suitable continuous system involving either single screw or twin screw extrusion or heat exchangers together with either high shear or static mixing. Any process can be envisioned such that the polymer is ultimately dissolved in the presence of water, the surfactant(s), the plasticizer, and other optional ingredients including stepwise processing via pre-mix portions of any combination of ingredients.

The processing mixtures of the present invention comprise: from about 15% to about 60% solids, in one embodiment from about 20% to about 55% solids, in another embodiment from about 25% to about 50% solids, and in yet another embodiment from about 30% to about 45% solids by weight of the processing mixture before drying; and have a viscosity of from about 2,500 cps to about 150,000 cps, in one embodiment from about 5,000 cps to about 100,000 cps, in another embodiment from about 7,500 cps to about 75,000 cps, and in still another embodiment from about 10,000 cps to about 60,000 cps.

The % solids content is the summation of the weight percentages by weight of the total processing mixture of all of the solid, semi-solid and liquid components excluding water and any obviously volatile materials such as low boiling alcohols. The processing mixture viscosity values are measured using a TA Instruments AR500Rheometer with 4.0 cm diameter parallel plate and 1,200 micron gap at a shear rate of 1.0 reciprocal seconds for a period of 30 seconds at 23° C.

B. Aeration of Processing Mixture

The aeration of the processing mixture is accomplished by introducing a gas into the mixture. In one embodiment this is done by mechanical mixing energy. In another embodiment this may be achieved via chemical means. The aeration may be accomplished by any suitable mechanical processing means, including but not limited to: (i) Batch tank aeration via mechanical mixing including planetary mixers or other suitable mixing vessels, (ii) semi-continuous or continuous aerators utilized in the food industry (pressurized and non-pressurized), or (iii) spray-drying the processing mixture in order to form aerated beads or particles that can be compressed such as in a mould with heat in order to form the porous solid.

In a particular embodiment, it has been discovered that the hair care article can be prepared within continuous pressurized aerators that are conventionally utilized within the foods industry in the production of marshmallows. Suitable continuous pressurized aerators include the Morton whisk (Morton Machine Co., Motherwell, Scotland), the Oakes continuous automatic mixer (E.T. Oakes Corporation, Hauppauge, N.Y.), the Fedco Continuous Mixer (The Peerless Group, Sidney, Ohio), and the Preswhip (Hosokawa Micron Group, Osaka, Japan).

Less preferred, but also envisioned in aeration with chemical foaming agents by in-situ gas formation (via chemical reaction of one or more ingredients, including formation of carbon dioxide ($CO_2$ (g)) by an effervescent system. An additional possibility is aeration via volatile blowing agents such as low boiling hydrocarbons including, but not limited to, isopentane, pentane, isobutene etc.

In one embodiment, the pre-mixture is pre-heated immediately prior to the aeration process at above ambient temperature but below any temperatures that would cause degradation of the component. In one embodiment, the pre-mixture is kept at above about 40° C. and below about 99° C., in another embodiment above about 50° C. and below about 95° C., in another embodiment above about 60° C. and below about 90° C. In one embodiment, when the viscosity at ambient temperature of the pre-mix is from about 15,000 cps to about 150,000 cps, the optional continuous heating should be utilized before the aeration step. In another embodiment, additional heat is applied during the aeration process to try and maintain an elevated temperature during the aeration. This can be accomplished via conductive heating from one or more surfaces, injection of steam or other processing means.

In one embodiment the wet density range of the aerated pre-mixture ranges from about 0.12 g/cm$^3$ to about 0.50 g/cm$^3$, in another embodiment from about 0.15 g/cm$^3$ to about 0.45 g/cm$^3$, in another embodiment from about 0.20 g/cm$^3$ to about 0.40 g/cm$^3$, and in yet another embodiment from about 0.25 g/cm$^3$ to about 0.35 g/cm$^3$.

C. Forming the Aerated Wet Processing Mixture

The forming of the aerated wet processing mixture may be accomplished by any suitable means to form the mixture in a desired shape or shapes including, but not limited to (i) depositing the aerated mixture to moulds of the desired shape and size comprising a non-interacting and non-stick surface including aluminium, Teflon, metal, HDPE, polycarbonate, neoprene, rubber, LDPE, glass and the like; (ii) depositing the aerated mixture into cavities imprinted in dry granular starch contained in a shallow tray, otherwise known as starch moulding forming technique; and (iii) depositing the aerated mixture onto a continuous belt or screen comprising any non-interacting or non-stick material Teflon, metal, HDPE, polycarbonate, neoprene, rubber, LDPE, glass and the like which may be later stamped, cut, embossed or stored on a roll.

D. Drying the Aerated Wet Processing Mixture into a Porous Dissolvable Solid Substrate The drying of the formed aerated wet processing mixture may be accomplished by any suitable means including, but not limited to (i) drying room(s) including rooms with controlled temperature and pressure or atmospheric conditions; (ii) ovens including non-convection or convection ovens with controlled temperature and optionally humidity; (iii) Truck/Tray driers, (iv) multi-stage inline driers; (v) impingement ovens; (vi) rotary ovens/driers; (vii) inline roasters; (viii) rapid high heat transfer ovens and driers; (ix) dual plenum roasters, and (x) conveyor driers, and combinations thereof. Any suitable drying means that does not comprise freeze-drying can be used.

The drying temperature may range from about 40° C. to about 200° C. In a preferred embodiment, the drying environment is heated to a temperature between 100° C. and 150° C. In one embodiment, the drying temperature is between 105° C. and 145° C. In another embodiment, the drying temperature is between 110° C. and 140° C. In a further embodiment, the drying temperature is between 115° C. and 135° C.

Other suitable drying environments include "volumetric heating" techniques using high frequency electromagnetic fields such as Microwave Drying and Radio Frequency (RF) Drying. With these techniques, the energy is transferred electromagnetically through the aerated wet pre-mixture rather than by conduction or convection.

Optional ingredients may be imparted during any of the above described four processing steps or even after the drying process.

E. Preparing the Surface Resident Coating Comprising the Cationic Surfactant Conditioner Active The preparation of the surface resident coating comprising the cationic surfactant conditioner active may include any suitable mechanical or otherwise physical means to produce a particulate composition comprising the cationic surfactant conditioner active as described herein. In a preferred embodiment, the pure cationic surfactant material in either pellet or granular or other solid-based form (and comprising any minor impurities as supplied by the supplier including residual solvents and plasticizers) is ground into a fine powder via a variety of mechanical means, for instance in a grinder. In some embodiments, it is helpful to include inert fillers within the grinding process, for instance aluminum starch octenylsuccinate under the trade name DRY-FLO® PC and available from Akzo Nobel DryFlow® starch, at a level sufficient to improve the flow properties of the powder and to mitigate inter-particle sticking or agglomeration during powder production or handling. Other optional excipients or cosmetic actives, as described herein, can be incorporated into the powder during the grinding process. The resulting powder may also be blended with other inert powders, either of inert materials or other powder-active complexes as described herein.

F. Combining Surface Resident Coating comprising the Cationic Surfactant Conditioner Actives with the Porous Dissolvable Solid Substrate Any suitable application method can be used to apply the surface resident coating comprising the cationic surfactant conditioner active to the porous dissolvable solid substrate such that it forms a cationic conditioner active as part of the hair care article. For instance, the porous dissolvable solid substrate can have a tacky surface by drying the dissolvable porous solid to a specific water content) before application of powder to facilitate the adherence of the surface resident coating comprising the cationic surfactant conditioner active to the porous dissolvable solid substrate. In one embodiment, the dissolvable porous solid substrate is dried to a moisture content of from about 0.1% to about 25%, in one embodiment from about 3% to about 25%, in another embodiment from about 5% to about 20% and in yet another embodiment from about 7% to about 15%. Alternatively, a previously-dried porous dissolvable solid substrate's surface can be made to reversibly absorb a controlled level of atmospheric moisture prior to application of the powder within a controlled humidity environment for a specific period of time until equilibrium is achieved. In one embodiment, the humidity environment is controlled from about 20% to about 85% relative humidity; in another embodiment, from about 30% to about 75% relative humidity; and in yet another embodiment, from about 40% to about 60% relative humidity.

In another embodiment, the porous dissolvable solid substrate is placed in a bag, tray, belt, or drum containing or otherwise exposed to the powder and agitated, rolled, vibrated or shaken to apply and distribute the powder, either in a batch or continuous production manner. The surface resident coating comprising the cationic surfactant conditioner active can be applied over portions or entire regions of the porous dissolvable solid substrate's exterior surface, and can be applied in a manner to adorn, decorate, form a logo, design, etc.

V. Test Methods

A. Dissolution Rate

The hair care article of present invention has a Dissolution Rate that allows the hair care article to rapidly disintegrate during use application with water. The Dissolution Rate of the hair care article is determined in accordance with the methodology described below.

Hand Dissolution Method: 0.5 to 1.5 g (approximately 10 to 20 square centimeters if in a 3 to 10 mm thick sheet/pad form) of the hair care article (as described in the examples herein) is placed in the palm of the hand while wearing nitrile gloves, 7.5 cm$^3$ of warm tap water (from about 30° C. to about 35° C.) is quickly applied to the hair care composition via syringe. Using a circular motion, palms of hands are rubbed together 2 strokes at a time until dissolution occurs (up to 30 strokes). The hand dissolution value is reported as the number of strokes it takes for complete dissolution or as 30 strokes as the maximum. For the latter scenario, the weight of the undissolved material is also reported.

The hair care articles of the present invention have a hand dissolution value of from about 1 to about 30 strokes, in one embodiment from about 2 to about 25 strokes, in another embodiment from about 3 to about 20 strokes, and in still another embodiment from about 4 to about 15 strokes.

B. Thickness

The thickness of the hair care article and/or the porous dissolvable solid substrate is obtained using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1 inch diameter platen weighing about 32 grams, which measures thickness at an application pressure of about 40.7 phi (6.32 gm/cm$^2$).

The thickness of the hair care article and/or the porous dissolvable solid substrate is measured by raising the platen, placing a section of the sample on the stand beneath the platen, lowering the platen to contact the sample, releasing the platen, and measuring the thickness of the sample in millimeters on the digital readout. The sample should be fully extended to all edges of the platen to make sure thickness is measured at the lowest possible surface pressure, except for the case of more rigid samples which are not flat. For more rigid samples which are not completely flat, a flat edge of the sample is measured using only one portion of the platen impinging on the flat portion of the sample. In the case of cylindrical, spherical, or other objects with more of a third dimension versus a pad or strip, the thickness is taken as the maximum distance of the shortest dimension, i.e., the diameter of a sphere or cylinder for instance, and the thickness ranges are the same as described above.

C. Basis Weight

The Basis Weight of the hair care article and/or the porous dissolvable solid substrate is calculated as the weight of the hair care article and/or the porous dissolvable solid substrate per area of the selected hair care article and/or the porous dissolvable solid substrate (grams/m$^2$). The area is calculated as the projected area onto a flat surface perpendicular to the outer edges of the hair care article and/or the porous dissolvable solid substrate. For a flat object, the area is thus computed based on the area enclosed within the outer perimeter of the sample. For a spherical object, the area is thus computed based on the average diameter as $3.14 \times (diameter/2)^2$. For a cylindrical object, the area is thus computed based on the average diameter and average length as diameter×length. For an irregularly shaped three dimensional object, the area is computed based on the side with the largest outer dimensions projected onto a flat surface oriented perpendicularly to this side.

D. Solid Density

The porous dissolvable solid substrate of the personal care compositions described herein can be characterized in terms of a solid density determination.

The solid density of the porous dissolvable solid substrate can be determined by dividing the weight of the solid by the known volume of the solid. The latter can be determined by a number of techniques including producing the solid within a mold of known x-y dimensions and measuring the resulting thickness to account for any shrinkage or expansion during the drying process. The solid can also be cut to known x-y dimensions, i.e., by using a circular or square cutting die of known diameter or dimensions and then by measuring the thickness. Alternatively, in the instances where there are not any significant thickness variations, the density can be calculated by the equation: Calculated Density=Basis Weight of porous solid/(Average porous Solid Thickness×1,000).

E. Cell Inter-connectivity

The hair care article and/or the porous dissolvable solid substrate of the present invention have a high degree of cell inter-connectivity, i.e., are predominantly open-celled solid foams as opposed to being predominantly closed-cell solid foams. The cell inter-connectivity can be assessed by light microscopy, scanning electron microscopy, micro computed tomography imaging parameters (Star Volume and SMI Index), gas pyncnometry parameters (% Open Cells), or other suitable methodology.

A qualitative method of determining cell inter-connectivity is via light microscopy. This is performed by cutting a 2-3 mm wide sliver of the hair care article and/or the porous dissolvable solid substrate in the z-direction using scissors or a sharp blade, measured across the normal x-y largest surface, and turning the resulting sliver by 90 degrees to reveal the internal cellular structure of the freshly cut cross-sectional area. This cross-sectional area can be assessed by close visual inspection or, more accurately, by employing magnification under a stereo microscope such as the SZX12 Stereo microscope available from Olympus Olympus America Inc., Center Valley, Pa. The open-celled hair care article and/or the porous dissolvable solid substrate of the present invention can easily be identified by examining the inner portion of the cross-sectional area which will comprise a predominantly three dimensional network of struts with open void spaces surrounding the struts that are inter-connected to one another including in the third dimension through the depth of the cross-section. In contrast, the inner cross-section of a closed-cell foam will appear as discrete bubbles that are cut across and then only being inter-connected at the cross-sectional surface in two dimensions by virtue of the cutting process employed to generate the exposed cross-sectional area.

Another means to determine the cell interconnectivity is via the Star Volume and the Structure Model Index. Disk-like samples, approximately 4 cm in diameter and 3 to 7 mm high, are scanned using a micro computed tomography system (μCT80, SN 06071200, Scanco Medical AG). Each sample is imaged while sitting flat on the bottom of a cylindrical tube. Image acquisition parameters are 45 kVp, 177 μA, 51.2 mm field of view, 800 ms integration time, 1000 projections. The number of slices is adjusted to cover the height of the sample. The reconstructed data set consisted of a stack of images, each 2048×2048 pixels, with an isotropic resolution of 25 μm. For data analysis, a volume of interest is selected to be fully within the sample, avoiding the surface region. A typical volume of interest is 1028×772×98 voxels.

Structure Model Index (SMI) is measured using Scanco Medical's Bone Trabecular Morphometry evaluation with a threshold of 17. With this index the structural appearance of trabecular bone is quantified (see T. Hildebrand, P. Rüegsegger. Quantification of bone microarchitecture with the structure model index. *Comp Meth Biomech Biomed Eng* 1997; 1:15-23). The triangulated surface is dilated in normal direction by an infinitesimal amount, and the new bone surface and volume is calculated. By this, the derivative of the bone surface (dBS/dr) can be determined. The SMI is then represented by the equation:

$$SMI = 6 \cdot \frac{BV \cdot \frac{dBS}{dr}}{BS^2}$$

SMI relates to the convexity of the structure to a model type. Ideal (flat) plates have an SMI of 0 (no surface change with dilation of the plates), whereas ideal cylindrical rods have an SMI of 3 (linear increase in surface with dilation of rods). Round spheres have an SMI of 4. Concave structure gives negative dBS/dr, resulting in negative SMI values. Artificial boundaries at the edge of the volume of interest are not included in the calculation and thus suppressed.

In addition to the Scanco Medical Analysis, StarVolume measurements are made. Star Volume is a measure of the "openness" of the void space in a two phase structure. By choosing a random uniformly distributed set of points in the phase of interest (in our case this is the background), we can extend lines in random directions from each of these points. The lines are extended until they touch the foreground phase. The length of each of these lines is then recorded. The random points have a sampling of 10 in each direction (x/y/z) and at each point 10 random angles are chosen. If the line extends to the border of the ROI of interest that line is discarded (we only want to accept lines that actually intersect with the foreground phase). The final equation is based upon the research published in *Star volume in bone research. A histomorphometric analysis of trabecular bone structure using vertical sections*; Vesterby, A.; Anat Rec.; 1993 February; 235(2):325-334.:

$$StarVolume = \frac{4}{3}\pi \cdot \frac{\sum dist^3}{N}$$

where "dist" is the individual distances and N is the number of lines examined.

The Percent Open Cell Content is measured via gas pycnometry. Gas pycnometry is a common analytical technique that uses a gas displacement method to measure volume accurately. Inert gases, such as helium or nitrogen, are used as the displacement medium. The sample is sealed in the instrument compartment of known volume, the appropriate inert gas is admitted, and then expanded into another precision internal volume. The pressure before and after expansion is measured and used to compute the sample volume. Dividing this volume into the sample weight gives the gas displacement density.

ASTM Standard Test Method D2856 provides a procedure for determining the percentage of open cells using an older model of an air comparison pycnometer. This device is no longer manufactured. However, you can determine the percentage of open cells conveniently and with precision by performing a test which uses Micromeritics' AccuPyc Pycnometer. The ASTM procedure D2856 describes 5 methods (A, B, C, D, and E) for determining the percent of open cells of foam materials.

For these experiments, the samples can be analyzed using an Accupyc 1340 using nitrogen gas with the ASTM foampyc software. Method C of the ASTM procedure is to be used to calculate to percent open cells. This method simply compares the geometric volume as determined using calipers and standard volume calculations to the true volume as measured by the Accupyc. It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde On and Paul Webb.

F. Cell Wall Thickness

The Cell Wall Thickness of the hair care article and/or the porous dissolvable solid substrate is computed from the scanned images via a micro computed tomography system (μCT80, SN 06071200, Scanco Medical AG) as described herein. The Cell Wall Thickness is determined according to the method defined for the measurement of Trabecular Thickness using Scanco Medical's Bone Trabecular Morphometry evaluation. The definition of Trabecular Thickness as taken from the Scanco User's manual: Trabecular Thickness uses a Euclidean distance transformation (EDM), which calculates the Euclidean distance from any point in the foreground to the nearest background point. The Trabecular Thickness measure represents twice the centerline values associated with the local maxima of the EDM, which represents the distance to the center of the object (twice this distance will yield the thickness).

G. Specific Surface Area

The Specific Surface Area of the hair care article and/or the porous dissolvable solid substrate is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the degassed sample+sample tube weight. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved.

Sample Preparation (Degassing): A sample not adequately cleaned of adsorbed contaminants will outgas during an analysis and some portion of the surface will be inaccessible to measurement. The purpose of degassing is to remove these adsorbed molecules from the surface of the sample prior to analysis. Adsorptive molecules must reach all parts of the surface for the true surface area to be revealed. Samples are prepared by heating the sample while simultaneously evacuating the sample tube.

For these experiments, the samples are outguessed under evacuation at room temperature overnight. Samples may then analyzed using an ASAP 2420 with krypton gas adsorption. Krypton gas is preferred over nitrogen gas as it has a saturation pressure approximately 1/300 that of nitrogen at liquid nitrogen temperature (krypton: 2.5 torr; nitrogen: 760 torr). Therefore, compared to nitrogen, there is in the free space above the sample about 1/300 the number of krypton molecules present at the same relative pressure. Since about the same number of krypton and nitrogen molecules are required to form a monolayer, this number represents a far greater proportion of the quantity dosed than in the case of nitrogen. These measurements can be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde Orr and Paul Webb.

H. Evaluation of Surface Resident Coating Comprising a Cationic Surfactant Conditioning Active The presence of a surface resident coating comprising a cationic surfactant conditioning active of the present invention can be determined by a number of techniques. For detection of a particulate or powder coating, the surface of application as well as the cross-sections perpendicular to the larger surfaces of the porous dissolvable solid substrate can be examined by microscopic techniques. These microscopic techniques may include light microscopy and scanning electron microscopy (SEM). The light microscopy may include but are not necessarily limited to bright field, dark field, or confocal microscopy techniques. Other techniques for mapping unique elements such as silicon or distinctive functional groups such as quaternary ammonium groups on the cross-sectional surface include: time of flight secondary ion mass spectroscopy (ToF-SIMS), or infrared microscopy.

Potential methods for looking at the distribution of particles from the surface to the interior of the porous dissolvable solid substrate without sectioning the samples include: micro-Computed Tomography (micro-CT), Magnetic Resonance Imaging (MRI), Acoustic Imaging, Confocal Fluorescence Microscopy, Confocal Raman Spectroscopy, and Confocal Infrared Reflectance Spectroscopy.

The determination of surface-resident coating particles on cross-sectioned porous dissolvable solid substrate can be performed by comparing the distribution of the particles across the cut cross-section of the porous solid. Specifically, the surface resident coating particles should be present at the original solid/air interfaces, but not within the exposed cross sectioned interior of the solid cell walls as can be ascertained by analyzing the exposed freshly cut cross-sectional interiors of the solid. It should be noted that some contamination of the freshly cut cross-sectional solid cell wall interiors may occur as a consequence of the cutting process of the porous solid. However, the preponderance (in one embodiment, from about 50% to about 100%) of the surface resident coating particle distribution will occur at the original solid/air interfaces and not within the exposed cut cross-sectional interiors of the cell walls.

It should also be noted that the surface resident coating particles of the present invention generally do not spread uniformly across all exposed solid/air interfaces. Rather, it has been found that the surface resident coatings of the present invention typically spread, from the point of coating application, into cavities down to about 0.5 to about 3.0 mm according to gravity. Accordingly, the determination of surface resident particles of cosmetic actives of the present invention (as described above), should be conducted across many different cross sections from top-to-bottom and from edge-to-edge of the porous solid. If present, the surface resident cosmetic active particle will generally be within the regional vicinity (to within about 0.5 to about 3.0 mm from the surface) of the surface to where the cosmetic active was first applied.

I. Wet and Dry Combing Evaluation

The wet and dry combing performance is assessed using a qualitative panel of 10 trained graders. Two controls are included in each test encompassing applying a clarifying shampoo (Pantene Pro-V Clarifying Shampoo, distributed by Procter & Gamble, Cincinnati Ohio) and a two step application of the same clarifying shampoo followed by application of a separate hair conditioner (Pantene Pro-V Always Smooth Conditioner, distributed by Procter & Gamble, Cincinnati Ohio). In a typical test 8 separate formulations can be assessed for their performance relative to the controls. The substrate is virgin brown hair obtainable from a variety of sources that is screened to ensure uniformity and lack of meaningful surface damage.

Five 8 inch length hair switches (4 grams each) are combined in a hair switch holder, wet with manipulation for ten seconds with water at 40 C and moderate water hardness (9 to 10 grains per gallon) to ensure even wetting. The switch is deliquored lightly and product is applied uniformly over the length of the combined switches from inch below the holder towards the end at a level of 0.1 gram of product per one gram of dry hair (or 2 grams of product for the combined 20 grams of hair in the holder). The combined switches are lathered by a rubbing motion typical of that used by consumers for 30 seconds and rinsed with water flowing at 1.5 gallons per minute at 40 C (with the hair being manipulated) for 30 seconds to ensure rinsing completeness. This step is then repeated. The above is the protocol used to apply the clarifying shampoo control. For the two step application of the same clarifying shampoo followed by application of a separate hair conditioner, the conditioner is subsequently applied in the same manner as the clarifying shampoo above, but the conditioner application is only done once and not repeated as in the case for the clarifying shampoo.

Wet and dry combing evaluations are obtained using trained graders. The above freshly prepared wet switches are stored within aluminum foil until just prior to wet combing grading. The switches are hung on a metal rod rack with one switch from each treatment included in the grading set. Two consumers are asked to grade each switch with the first consumer firstly detangling the wet switch with the narrow end of a narrow tooth nylon comb (typical of those used by consumers) prior to combing evaluation. The graders are asked to compare the treatments (labeled A through J) for wet combing by combing the switch with the nylon comb in a downward manner and rate the ease/difficulty of combing on a zero to ten point scale. The graders are informed of which two treatments represent the controls (A & B) prior to the evaluation for calibration purposes. The order of the treatments (A through J) is randomized between the differing graders. The grades are averaged across the 10 consumers for each treatment to give the average and 95% confidence groupings are then computed from the means employing Fisher's lease significant difference (LSD) procedure via the StatAdvisor™ feature of Statgraphics software (Statpoint Technologies, Inc., Warrenton, Va.). The means are then computed as a normalized percentage by the following equation:

$$\frac{(Mean_{Treatment} - Mean_{Clarifying})}{(Mean_{Clarifying/Conditioner} - Mean_{Clarifying})} \times 100\%$$

For dry combing evaluations, the hair switches are then moved into a controlled temperature (hung on racks) and humidity room (72 F/50% RH) and allowed to dry overnight. The graders are then asked to evaluate dry combing performance using the nylon comb for ease/difficulty of combing on a zero to ten point scale in an analogous manner to the above wet combing evaluations. The grading data is computed and analyzed as described above for the wet combing data.

J. Silicone Deposition on Hair

The hair switches are cut for deposition testing. Silicone is extracted from 1.5 g of hair with 6 mL of 50:50 toluene: methylisobutyl ketone in 20 mL scintillation vials. The vials are agitated on a pulsed vortexer for 30 minutes. The silicone of the extract is quantified using inductively coupled plasma optical emission spectrometry (ICP-OES). ICP calibration standards of known silicone concentration are made using the same or a structurally comparable type of silicone raw material as the products being tested. The working range of the method is 8-2300 μg silicone per gram of hair.

K. Quaternized Alkyl Conditioner Deposition on Hair

The hair switches are cut for deposition testing. Quaternary surfactant is extracted from 1.5 g of hair with 15 mL of 20:20:60 methylisobutyl ketone:methanol: hexane in 20 mL scintillation vials. The vials are agitated on a pulsed vortexer for 30 minutes. 500 μL of the extracts are transferred to 2 mL autosampler vials and evaporated to dryness under a gentle stream of nitrogen. The samples are reconstituted with 100 μL of methanol. Quaternary surfactant in the extracts is quantified using reversed phase HPLC on a Waters XBridge C8 column with a trifluoroacetic acid/methanol gradient and evaporative light scattering detection. Calibration standards of known quaternary surfactant concentration are made using the same surfactant raw material as the products being tested. The working range of the method is roughly 50-500 μg quaternary surfactant per gram of hair.

L. Fatty Alcohol Deposition on Hair

The hair switches are cut for deposition testing. Fatty alcohol is extracted from 1.5 g of hair with 15 mL of 20:20:60 methylisobutyl ketone:methanol: hexane in 20 mL scintillation vials. The vials are agitated on a pulsed vortexer for 30 minutes. 1 mL of the extracts is transferred to 2 mL autosampler vials and evaporated to dryness under a gentle stream of nitrogen. The samples are reconstituted with 500 μt of Sylon BFT in dichloromethane. Fatty alcohol in the extracts is quantified using GC/FID with a nonadecanol internal standard and commercially available fatty alcohol standards. The working range of the method is roughly 6-6000 μg fatty alcohol per gram of hair.

IV. Methods of Use

The compositions of the present invention may be used for treating mammalian keratinous tissue such as hair and/or scalp, and provide rapid rinse-ability. The method for conditioning the hair may comprise the steps of: a) applying an effective amount of the hair care product to the hand, b) wetting the hair care product with water and rubbing to dissolve the solid, c) applying the dissolved material to either the hair or scalp such as to treat, and d) rinsing the diluted treatment from the hair or scalp using water. These steps can be repeated as many times as desired to achieve the desired treatment benefit.

V. Examples

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Example 1

Preparation of Liquid Processing Mixture

The following surfactant/polymer liquid processing compositions are prepared at the indicated weight percentages as described below.

| Component | Ex. 12 |
|---|---|
| Glycerin | 3.2 |
| Polyvinyl alcohol[1] | 8.1 |
| Sodium Lauroamphoacetate (26% activity)[2] | 31.8 |
| Ammonium Laureth-3 sulfate (25% activity) | 4.9 |

-continued

| Component | Ex. 12 |
|---|---|
| Ammonium Undecyl sulfate (24% activity) | 19.9 |
| Ammonium Laureth-1 sulfate (70% activity) | 8.0 |
| Cationic cellulose[3] | 0.5 |
| Citric Acid | 1.6 |
| Distilled water | 22.0 |
| Total | 100.0 |
| pH | 5.8 |
| Viscosity (cp) | 35,400 |

[1]Sigma-Aldrich Catalog No. 363081, MW 85,000-124,000, 87-89% hydrolyzed
[2]McIntyre Group Ltd, University Park, IL, Mackam HPL-28ULS
[3]UCARE ™ Polymer LR-400, available from Amerchol Corporation (Plaquemine, Louisiana)

A target weight of 300 grams of the above composition is prepared using a conventional overhead stirrer (IKA® RW20DZM Stirrer available from IKA® Works, Inc., Wilmington, Del.) and a hot plate (Corning Incorporated Life Sciences, Lowell, Mass.). The distilled water and glycerin are added into a vessel with stirring at 100-150 rpm. The cationic polymer, when present, is then slowly added with constant stirring until homogenous. The polyvinyl alcohol is weighed into a suitable container and slowly added to the main mixture in small increments using a spatula while continuing to stir while avoiding the formation of visible lumps. The mixing speed is adjusted to minimize foam formation. The mixture is slowly heated to 80° C. after which surfactants are added. The mixture is then heated to 85° C. while continuing to stir and then allowed to cool to room temperature. Additional distilled water is added to compensate for water lost to evaporation (based on the original tare weight of the container). The final pH is between 5.2-6.6 and adjusted with citric acid or diluted sodium hydroxide if necessary. The resulting processing mixture viscosity is measured.

Example 2

Preparation of Open-Celled Porous Dissolvable Solid Shampoo Substrate

An open-celled Porous Dissolvable Solid Shampoo Substrate was prepared from the liquid processing mixture from Examples 1 as described below.

| | |
|---|---|
| Aeration Time (sec) | 62 |
| Wet Density (g/cm$^3$) | 0.26 |
| Oven Temperature (° C.) | 130 |
| Drying Time (min) | 38 |
| Average dry substrate weight (g) | 1.10 |
| Average dry substrate thickness (cm) | 0.62 |
| Average substrate shrinkage (%) | 4.6% |
| Average dry substrate density (g/cm$^3$) | 0.11 |
| Average basis weight (g/m$^2$) | 650 |

300 grams of the processing mixture (from Examples 1) is stored within a convection oven for greater than two hours at 70° C. to pre-heat the processing mixture. The mixture is then transferred into a pre-heated 5 quart stainless steel bowl (by placing into 70° C. oven for greater than 15 minutes) of a KITCHENAID® Mixer Model K5SS (available from Hobart Corporation, Troy, Ohio) fitted with a flat beater attachment and with a water bath attachment comprising tap water at 70-75° C. The mixture is vigorously aerated at a maximum speed setting of 10 until a wet density of approximately 0.26 grams/cm$^3$ is achieved (time recorded in table). The density is measured by weighing a filling a cup with a known volume and evenly scraping off the top of the cup with a spatula. The resulting aerated mixture is then spread with a spatula into square 160 mm×160 mm aluminum molds with a depth of 6.5 mm with the excess wet foam being removed with the straight edge of a large metal spatula that is held at a 45° angle and slowly dragged uniformly across the mold surface. The aluminum molds are then placed into a 130° C. convection oven for approximately 35 to 45 minutes. The molds are allowed to cool to room temperature with the substantially dry porous solids removed from the molds with the aid of a thin spatula and tweezers.

Each of the resulting 160 mm×160 mm square substrates in pad form is cut into nine 43 mm×43 mm squares (with rounded edges) using a cutting die and a Samco SB20 cutting machine (each square representing surface area of approximately 16.9 cm$^2$). The resulting smaller substrates are then equilibrated overnight (14 hours) in a constant environment room kept at 70° F. and 50% relative humidity within large zip-lock bags that are left open to the room atmosphere. Each substrate is then weighed and placed on an individual weight boat with the original mold side facing downward. The average substrate weights are recorded and the basis weight computed by dividing the average substrate weight by 0.00169 square meters. The resulting substrate thickness is measured with a digital caliper and recorded.

Example 3

Preparation of Quaternized Conditioner Powders

Two representative quaternized conditioner powders were prepared via grinding the original pellets within a small Black & Decker® coffee mill with repeated pulses spanning 2 to 3 minutes (approximately 10 grams per powder preparation). The representative quaternized conditioners chosen include stearoyltrimethylammonium chloride (STMAC) and distearoyldimethylammonium chloride (DSDMAC) available from Clariant Corporation (Charlotte, N.C.) as GENAMIN STAC and GENAMIN DSAP, respectively. The former had an activity of approximately 79.1% and the latter of approximately 92.4% activity. Due to the increased stickiness of the latter GENAMIN DSAP it was mixed 80:20 with corn starch (available from National Starch as DRY-FLO PC) prior to being ground.

Example 4

Structural Characterization of Porous Dissolvable Solid Shampoo Substrate

Figure 5:
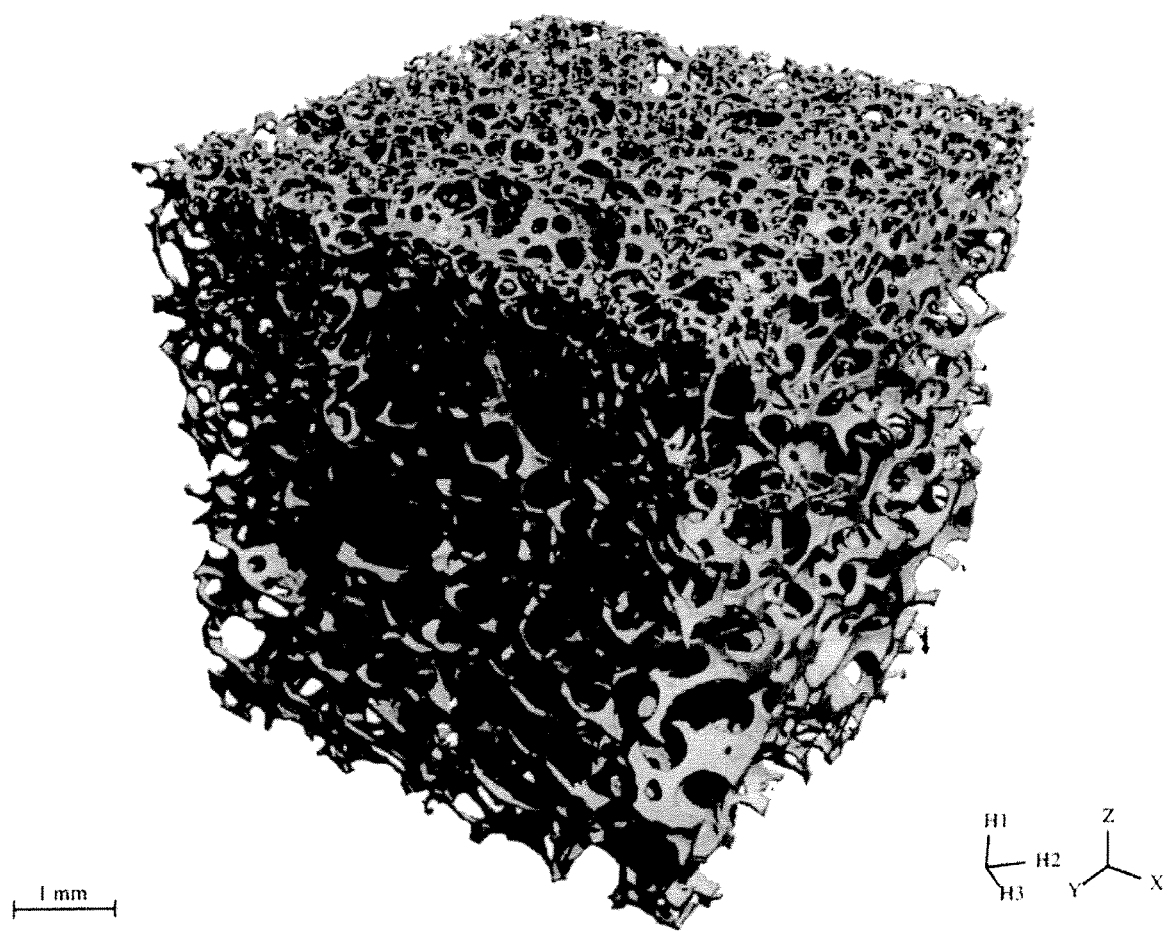
FIG. 5 is a Micro-CT 3-D Image of a porous dissolvable solid substrate.

The below tables summarize the structural measurements and qualitative physical integrity ratings taken on the Porous Dissolvable Solid Shampoo Substrate of Example 3. SEM and micro-CT images were also taken for the lower density Articles and are referenced in the attached FIGS. 5-6. The data was collected by the methods as described herein.

TABLE 1

Structural Measurements

Figure 6:
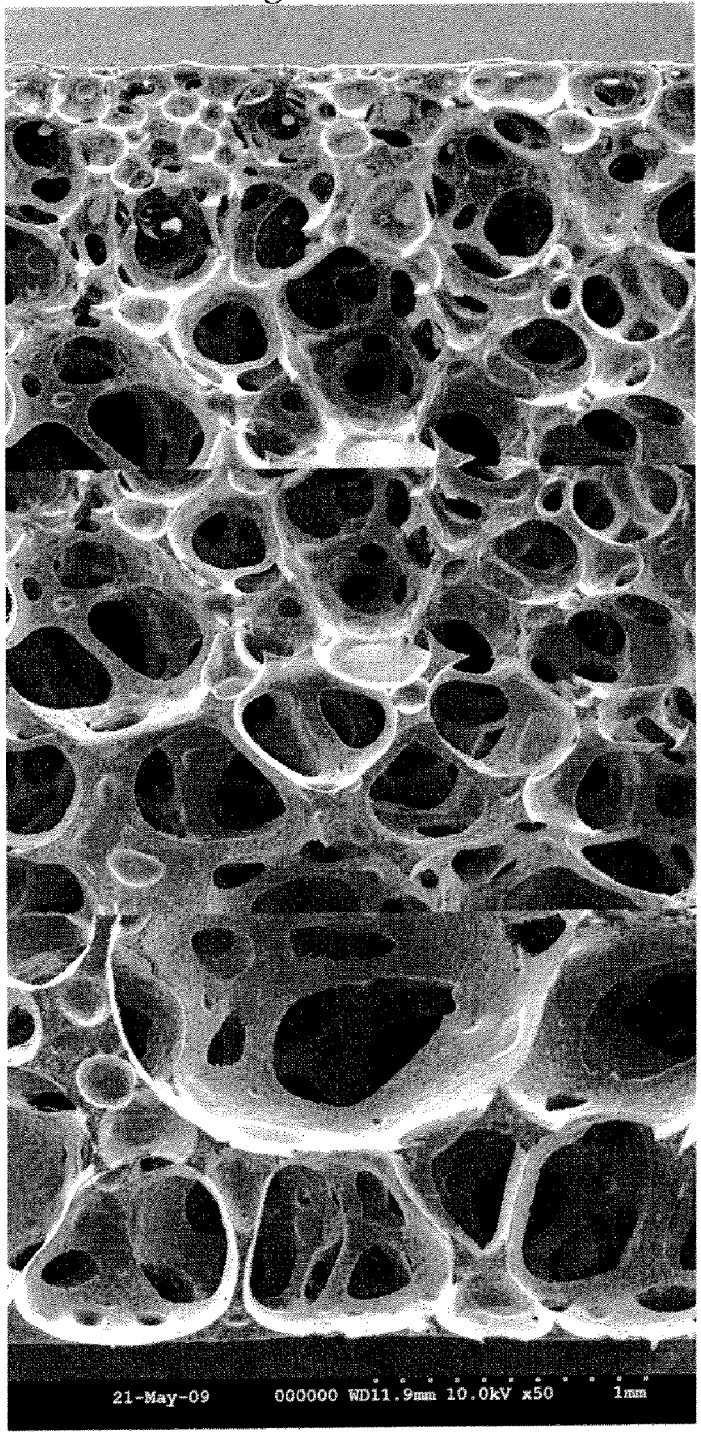
FIG. 6 is a Super-imposed Cross-Sectional SEM Images of Top-Middle-Bottom Regions of a porous dissolvable solid substrate.

| Example | Kr BET Surface Area (m²/g) | Pycnometry % Open Cells | Micro-CT Cell Wall thickness (mm) | Micro-CT Star Volume (mm³) | Micro-CT SMI Index | SEM Image | μCT Image |
|---|---|---|---|---|---|---|---|
| Ex. 3 | 0.036 | 89.1% | 0.074 | 5.1 | 1.5 | FIG. 6 | FIG. 7 |

The above data and referenced images demonstrate the Porous Dissolvable Solid Shampoo Substrate of Example 3 to be predominantly open-celled and exhibits fast dissolution performance (6 to 8 strokes) within the simulated hand dissolution protocol as described herein.

Example 5

Wet & Dry Combing and Deposition Data

The wet & dry combing evaluations are conducted with relative comparisons being made to the i) one step Clarifying shampoo control and ii) 2 step Clarifying shampoo plus separate hair conditioner control applications. To evaluate the influence of applied surface resident coatings of the quaternized powders from example 4 onto the Porous Dissolvable Solid Shampoo Substrate of example 3, it was assumed that two 16.9 square centimeter substrates of the Porous Dissolvable Solid Shampoo Substrate (approximately 2 to 2.2 grams of solid shampoo per two squares) would constitute a single dose for application to 150 grams of hair. For application to 20 grams of hair according to the wet & dry combing protocol this was scaled down to approximately 0.28 grams (0.28 grams of solid shampoo per 20 grams of hair) by cutting the substrates with scissors. Given that silicones are common for 2-in-1 conditioning shampoos, approximately 0.016 grams of an aminosilicone (available from Momentive, Performance Materials, Albany N.Y., Product code 65850 Y-14945 with a viscosity of 14,500 cps at 25° C. and an amine content of 0.050 meq/g) is coated onto the top surface of the cut piece (the side exposed to the atmosphere during the drying process and opposite the side in contact with the aluminum mold during production) with a positive displace micro-dispenser and allowed to soak into the open-celled surface for several hours. The respective STMAC and DSDMAC powders from Example 4 are then applied by coating the exposed surfaces of the cut piece (an iterational process whereby additional powder is coated and excess powder is removed by shaking the solid piece with a spatula) with the desired amount of powder which is expressed as a weight percentage of the original 0.29 g solid weight, e.g., powders applied at 7.1% of weight of solid corresponds to approximately 0.020 grams of powder being coated onto the 0.28 gram cut piece of solid shampoo (after the addition of 0.016 grams of aminosilicone). The 95% confidence groupings were computed from the means (prior to normalizing to a percentage) employing Fisher's lease significant difference (LSD) procedure via the StatAdvisor™ feature of Statgraphics software (Statpoint Technologies, Inc., Warrenton, Va.). The deposition data was measured as described herein.

TABLE 3

Wet Combing Data

| Ex. | | Wet Combing | 95% Significance |
|---|---|---|---|
| | Clarifying Shampoo Control | 0% | A |
| | Clarifying Shampoo + Separate Conditioner Control | 100% | D |
| | Ex. 3 Porous Dissolvable Solid Shampoo Substrate with Aminosilicone Control | 27% | A |
| 5a | Ex. 3 Porous Dissolvable Solid Shampoo Substrate with Aminosilicone plus STMAC powder coating (5.7% of weight of solid) | 54% | B |
| 5b | Ex. 3 Porous Dissolvable Solid Shampoo Substrate with Aminosilicone plus STMAC powder coatings (7.1% of weight of solid) | 57% | BC |
| 5c | Ex. 3 Porous Dissolvable Solid Shampoo Substrate with Aminosilicone plus STMAC powder coating (9.6% of weight of solid) | 65% | BC |
| 5d | Ex. 3 Porous Dissolvable Solid Shampoo Substrate with Aminosilicone plus STMAC powder coating (28% of weight of solid) | 77% | C |
| 5e | Ex. 3 Porous Dissolvable Solid Shampoo Substrate with Aminosilicone plus DSDMAP powder coating (7.1% of weight of solid) | 55% | B |

TABLE 4

Dry Combing Data

| Ex. | | Dry Combing | 95% Significance |
|---|---|---|---|
| | Clarifying Shampoo Control | 0% | A |
| | Clarifying Shampoo + Separate Conditioner Control | 100% | D |
| | Ex. 3 Porous Dissolvable Solid Shampoo Substrate with Aminosilicone Control | 28% | AB |
| 5a | Ex. 3 Porous Dissolvable Solid Shampoo Substrate with Aminosilicone plus STMAC powder coating (5.7% of weight of solid) | 40% | BC |
| 5b | Ex. 3 Porous Dissolvable Solid Shampoo Substrate with Aminosilicone plus STMAC powder coatings (7.1% of weight of solid) | 53% | C |
| 5c | Ex. 3 Porous Dissolvable Solid Shampoo Substrate with Aminosilicone plus STMAC powder coating (9.6% of weight of solid) | 57% | C |
| 5d | Ex. 3 Porous Dissolvable Solid Shampoo Substrate with Aminosilicone plus STMAC powder coating (28% of weight of solid) | 99% | D |
| 5e | Ex. 3 Porous Dissolvable Solid Shampoo Substrate with Aminosilicone plus DSDMAP powder coating (7.1% of weight of solid) | 40% | BC |

TABLE 5

Deposition Data

| Ex. | | Silicone Deposition (ppm hair) | Fatty Alcohol Deposition (ppm hair) | STMAC Deposition (ppm hair) | DSDMAC Deposition (ppm hair) |
|---|---|---|---|---|---|
| | Clarifying Shampoo Control | 8 +/− 1 | 44 +/− 3 | 0 | 0 |
| | Clarifying Shampoo + Separate Conditioner Control | 97 +/− 8 | 507 +/− 35 | 0 | 0 |
| 5a | Ex. 3 Porous Dissolvable Solid Shampoo Substrate with Aminosilicone plus STMAC powder coating (5.5% of weight of solid) | 57 +/− 37 | 70 +/− 32 | 330 +/− 4 | 0 |
| 5b | Ex. 3 Porous Dissolvable Solid Shampoo Substrate with Aminosilicone plus STMAC powder coatings (7.1% of weight of solid) | 24 +/− 4 | 56 +/− 28 | 349 +/− 10 | 0 |
| 5c | Ex. 3 Porous Dissolvable Solid Shampoo Substrate with Aminosilicone plus STMAC powder coating (9.6% of weight of solid) | 71 +/− 35 | 54 +/− 24 | 331 +/− 1 | 0 |
| 5d | Ex. 3 Porous Dissolvable Solid Shampoo Substrate with Aminosilicone plus STMAC powder coating (28% of weight of solid) | 142 +/− 53 | 43 +/− 1 | 344 +/− 10 | 0 |
| 5e | Ex. 3 Porous Dissolvable Solid Shampoo Substrate with Aminosilicone plus DSDMAP powder coating (7.1% of weight of solid) | 54 +/− 23 | 83 +/− 28 | 0 | 185 +/− 7 |

The above data demonstrates single variably that imparting a quaternary conditioner as a surface resident powder coating (at all levels tested—see legs 5a-5e) results in a significant improvement in both wet and dry conditioning relative to the original Porous Dissolvable Solid Shampoo Substrate (See Tables 3 and 4). The deposition data in Table 3 also demonstrate that the presence of the surface resident powder coatings of the quaternary conditioners results in significant levels of deposited quaternary conditioner onto the hair after treatment (See Table 5). The data demonstrates that strong hair conditioning performance can be achieved with a single step shampoo application and the conditioning benefit can approach the performance of the 2 step shampoo plus separate conditioner control (between about 40% to about 99% of the performance).

Example 6

Hair Switch Lather Evaluations of Porous Dissolvable Solid Substrate with Applied Quaternized Conditioner Surface Resident Coatings The hair switch lather evaluations are conducted with relative comparisons being made to the appropriate retail 2-in-1 conditioning shampoo (Pantene Pro-V Smooth and Sleek). To evaluate the applied surface resident coatings of the quaternized powders from example 4 onto the Porous Dissolvable Solid Shampoo Substrate of example 3, it was assumed that one 16.9 square centimeter substrate of the Porous Dissolvable Solid Shampoo Substrate (approximately 1.1 grams of solid shampoo per squares) would be applied to 100 grams of hair. This takes into account consumer habits in India wherein consumers typically apply approximately ½ of the sachet shampoo dosage in a first wash immediately followed by reapplication of the remaining ½ of the sachet in a repeat application. For application to 15 grams of hair according to the hair switch lather method protocol this was scaled down to approximately 0.165 grams (0.33 grams divided by 2) of solid shampoo per 15 grams of hair by cutting the substrates with scissors. Given that silicones are common for 2-in-1 conditioning shampoos, approximately 0.009 grams of an aminosilicone (available from Momentive, Performance Materials, Albany N.Y., Product code 65850Y-14945 with a viscosity of 14,500 cps at 25° C. and an amine content of 0.050 meq/g) is coated onto the top surface of the cut piece (the side exposed to the atmosphere during the drying process and opposite the side in contact with the aluminum mold during production) with a positive displace micro-dispenser and allowed to soak into the open-celled surface for several hours. The DSDMAC powder from Example 4 is then applied by coating the exposed surfaces of the cut piece (an iterational process whereby additional powder is coated and excess powder is removed by shaking the solid piece with a spatula) with the desired amount of powder which is expressed as a weight percentage of the original 0.165 g solid weight, e.g., powders applied at 5.5% of weight of solid corresponds to approximately 0.009 grams of powder being coated onto the 0.165 gram cut piece of solid shampoo (after the addition of 0.009 grams of aminosilicone). The deposition data was measured as described herein.

Hair Switch Lather Data

TABLE 6

Hair Switch Lather Data

| Ex. | | Switch Lather (Coconut Oil) | 95% Significance |
|---|---|---|---|
| | Liquid 2-in-1 Conditioner Shampoo Control (Pantene Pro-V, Smooth & Sleek) | 60 +/− 5 ml | A |
| | Ex. 3 Porous Dissolvable Solid Shampoo Substrate with Aminosilicone Control | 87 +/− 4 ml | B |
| 6a | Ex. 3 Porous Dissolvable Solid Shampoo Substrate with Aminosilicone plus DSDMAP powder coating (5.5% of weight of solid) | 90 +/− 12 ml | B |

The above data demonstrates single variably that imparting quaternary conditioner as a surface resident powder coating (at a level of 5.5% by weight of the original shampoo solid—see leg 6a) does not significantly affect the lathering performance of the resulting shampoo solid (See Table 6).

Example 7

Hand Dissolution Evaluation of Porous Dissolvable Solid Substrate with Applied Quaternized Conditioner Surface Resident Coatings The hand dissolution evaluations are conducted as described herein. To evaluate the influence of applied surface resident coatings of the quaternized powders from example 4 onto the Porous Dissolvable Solid Shampoo Substrate of example 3, it was assumed that one 16.9 square centimeter substrate of the Porous Dissolvable Solid Shampoo Substrate (approximately 1.1 grams of solid shampoo per square) would be dissolved in one hand prior to application to the hair by the simulated addition of water to the top of the substrate by the other hand that is cupped and filled with water. Given that silicones are common for 2-in-1 conditioning shampoos, approximately 0.06 grams of an aminosilicone (available from Momentive, Performance Materials, Albany N.Y., Product code 65850 Y-14945 with a viscosity of 14,500 cps at 25° C. and an amine content of 0.050 meq/g) is coated onto the top surface of some of the substrates as noted in the table below (the side exposed to the atmosphere during the drying process and opposite the side in contact with the aluminum mold during production) with a positive displace micro-dispenser and allowed to soak into the open-celled surface for several hours. The DSDMAC powder from Example 4 is then applied to some of the substrates as noted in the table below by coating the exposed surfaces of the substrate (by dipping both sides of the substrate into the free powder within a weigh boat and shaking off the excess powder until the desired weight is achieved) until 0.06 grams of DSDMAC powder is deposited as a coating which is approximately 5.5% by weight of the original solid substrate.

Hand Dissolution Data

TABLE 7

Hand Dissolution Data

| Ex. | | Hand Dissolution (Number of Strokes) |
|---|---|---|
| | Ex. 3 Porous Dissolvable Solid Shampoo Substrate Control | 4 to 6 strokes |
| | Ex. 3 Porous Dissolvable Solid Shampoo Substrate with Aminosilicone Control | 4 to 6 strokes |
| 7a | Ex. 3 Porous Dissolvable Solid Shampoo Substrate plus DSDMAP powder coating (5.5% of weight of solid) | 4 to 6 strokes |
| 7b | Ex. 3 Porous Dissolvable Solid Shampoo Substrate with Aminosilicone plus DSDMAP powder coating (5.5% of weight of solid) | 4 to 6 strokes |

The above data demonstrates that quaternary conditioner as a surface resident powder coating (at a level of 5.5% by weight of the original shampoo solid—see legs 7a and 7b) does not significantly affect the hand dissolution performance of the resulting shampoo solid (See Table 7).

Note that any actives and/or compositions disclosed herein can be used in and/or with the articles, and in particular the household care articles, disclosed in the following U.S. patent applications, including any publications claiming priority thereto: U.S. 61/229,981; U.S. 61/229,986; U.S. 61/229,990; U.S. 61/229,996; U.S. 61/230,000; and U.S. 61/230,004. Such articles may comprise one or more of the following: detersive surfactant; plasticizer; enzyme; suds suppressor; suds booster; bleach; bleach stabilizer; chelant; cleaning solvent; hydrotrope; divalent ion; fabric softener additive (e.g. quaternary ammonium compounds); nonionic surfactant; perfume; and/or a perfume delivery system. Such articles may be utilized in methods including, but not limited to: dosing into a washing machine to clean and/or treat fabric; dosing into a dishwasher to clean and/or treat cutlery; and dosing into water to clean and/or treat fabric and/or hard surfaces.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair care article comprising:
   a.) a porous dissolvable solid substrate comprising:
      i. from about 10% to about 75% by weight of an anionic surfactant;
      ii. from about 10% to about 50% by weight of a water-soluble polymer;
      iii. from about 1% to about 30% by weight of a plasticizer; and
   b.) a surface resident coating comprising from about 10% to about 100% by weight of one or more cationic surfactant conditioner actives;
   wherein the weight ratio of the porous dissolvable solid substrate to the surface resident coating is from about 110:1 to about 0.5:1, and
   wherein the porous dissolvable solid substrate comprises a percent open cell content from about 80% to about 100.0%.

2. The hair care article of claim 1, wherein the weight ratio of the porous dissolvable solid substrate to the surface resident coating is from about 20:1 to about 1:1.

3. The hair care article of claim 1, wherein the weight ratio of the porous dissolvable solid substrate to the surface resident coating is from about 10:1 to about 1.5:1.

4. The hair care article of claim 1, wherein the weight ratio of the porous dissolvable solid substrate to the surface resident coating is from about 7:1 to about 3:1.

5. The hair care article of claim 1, wherein the surface resident coating comprising the cationic surfactant conditioner active is a powder.

6. The hair care article of claim 1, wherein the cationic conditioner active is selected from alkyl quaternary ammonium salts, alkyl amine salts, and mixtures thereof.

7. The hair care article of claim 1, wherein the cationic conditioner active is an alkyl quaternary ammonium salt having the Formula I:

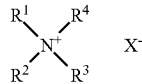

wherein $R^1$, $R^2$, $R^3$, and $R^4$ are each independently selected from the group consisting of an aliphatic group of from 1 to 22 carbon atoms, or an aromatic, alkoxy, polyoxyalkylene, alkylamido, hydroxyalkyl, aryl or alkylaryl group having up to 22 carbon atoms; and
wherein X is a salt-forming anion selected from the group consisting of halogen, acetate, citrate, lactate, glycolate, phosphate, nitrate, sulphate, alkylsulphate radicals, and combinations thereof.

8. The hair care article of claim 7, comprising the alkyl quaternary ammonium salt of Formula I, wherein $R^1$ and $R^2$ are each independently selected from the group consisting of $C_{16}$ to $C_{22}$ hydrocarbyl chains comprising at least one ester linkage in both $R^1$ and $R^2$, and $R^1$ and $R^2$ are each independently selected from $C_{16}$ to $C_{22}$ saturated or unsaturated chains, and wherein $R^3$ and $R^4$ are each independently selected from $CH_3$ and $CH_2CH_2OH$.

9. The hair care article of claim 1, wherein the cationic conditioner active is an alkyl amine salt corresponding to alkyl amines having the Formula II:

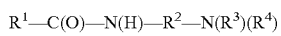

wherein $R^1$ is a fatty acid chain containing from 12 to 22 carbon atoms, $R^2$ is an alkylene group containing from one to four carbon atoms, and $R^3$ and $R^4$ are, independently, an alkyl group having from one to four carbon atoms.

10. The hair care article of claim 9, wherein the alkyl amine salt is the salt corresponding to alkyl amines having the Formula II neutralized with acids selected from the group consisting of hydrochloric acid, sulphuric acid, nitric acid, phosphoric acid, lactic acid, citric acid, tartaric acid, acetic acid, gluconic acid, glycolic acid and propionic acid, and combinations thereof.

11. The hair care article of claim 1, wherein the surface resident coating comprising the cationic surfactant conditioner active is in the of a layer.

12. The hair care article of claim 1, wherein the surface resident coating comprising the cationic surfactant conditioner active is attached to at least a portion of the outer surface of the porous dissolvable solid substrate.

13. The hair care article of claim 1, wherein the surface resident coating comprising the cationic surfactant conditioner active covers the outer surface of the porous dissolvable solid substrate.

14. The hair care article of claim 1, wherein the dissolvable hair care article comprises two porous dissolvable solid substrates, and wherein the surface resident coating comprising the cationic surfactant conditioner active is a layer situated between the two porous dissolvable solid substrates.

15. The hair care article of claim 1, wherein the porous dissolvable solid substrate having a basis weight of from about 125 grams/m² to about 3,000 grams/m² and a thickness of from about 0.5 mm to about 10 mm.

16. The hair care article of claim 1, wherein the porous dissolvable solid substrate comprises a specific surface area from about 0.03 m²/gram to about 0.25m²/gram.

17. The hair care article of claim 1, wherein the porous dissolvable solid substrate comprises a cell wall thickness of from about 0.02 mm to about 0.15 mm.

18. The hair care article of claim 1, wherein the hair care article comprises one or more water-soluble polymers selected from the group consisting of polyvinyl alcohols, polyacrylates, copolymers of acrylic acid and methacrylic acid, polyvinylpyrrolidones, polyalkylene oxides, starch and starch derivatives, pullulan, gelatin, hydroxypropylmethylcelluloses, methylcelluloses, and carboxymethycelluloses.

19. The hair care article of claim 1, wherein the hair care article comprises a plasticizer selected from the group consisting of polyols, copolyols, polycarboxylic acids, polyesters, and dimethicone copolyols.

20. The hair care article of claim 1, wherein the coating further comprises an additional component selected from the group consisting of a starch perfume matrix microsphere, a perfume loaded inorganic absorbent powder, a beta cyclodextrin encapsulated perfume, any other perfume active, an inactive starch composition, and any combination thereof.

21. A method for making a hair care article, the method comprising
　　applying a surface resident coating comprising the cationic surfactant conditioner active in powdered form to a porous dissolvable solid substrate comprising
　　　from about 10% to about 75% by weight of an anionic surfactant,
　　　from about 10% to about 50% by weight of a water-soluble polymer, and
　　　from about 1% to about 30% by weight of a plasticizer.

22. A method for making a hair care article, the method comprising:
　(a) preparing a processing mixture comprising from about 5% to about 50% by weight of a surfactant wherein the surfactant is selected from the group consisting of from about 0 to about 10% by weight of an anionic surfactant, non-ionic surfactant, polymeric surfactant, and combinations thereof, from about 5% to about 35% by weight of a water-soluble polymer, and from about 0.5% to about 20% by weight of a plasticizer;
　(b) aerating the processing mixture by introducing a gas into the processing mixture to form an aerated wet mixture;
　(c) forming the aerated wet mixture into one or more desired shapes;
　(d) drying the aerated wet mixture to form a porous dissolvable solid substrate;
　and; (e) applying a surface resident coating comprising the cationic surfactant conditioner active in powdered form to the porous dissolvable solid substrate.

23. The method of making a hair care article according to claim 22, wherein the surface resident coating comprising the cationic surfactant conditioner active is applied to the porous dissolvable solid substrate at a humidity of about 20% to about 70%.

24. The method of making a hair care article according to claim 22, wherein the surface resident coating comprising the cationic surfactant conditioner active is applied to the porous dissolvable solid substrate at a humidity of about 30% to about 60%.

25. The method of making a hair care article according to claim 22, wherein the surface resident coating comprising the inorganic particulate perfume complex is applied to the porous dissolvable solid substrate having a moisture content of about 5% to about 20%.

26. The method of making a hair care article according to claim 22, wherein the surface resident coating comprising the inorganic particulate perfume complex is applied to the porous dissolvable solid substrate having a moisture content of about 7% to about 15%.

* * * * *